(12) United States Patent
Baker et al.

(10) Patent No.: US 9,012,429 B2
(45) Date of Patent: Apr. 21, 2015

(54) METHODS AND COMPOSITIONS FOR THE PREVENTION OF AND TREATMENT OF INFECTIONS UTILIZING CHITOSAN-DERIVATIVE COMPOUNDS

(75) Inventors: Shenda Baker, Upland, CA (US); William P. Wiesmann, Washington, DC (US)

(73) Assignee: Synedgen, Inc., Claremont, CA (US)

( * ) Notice: Subject to any disclaimer, the term of this patent is extended or adjusted under 35 U.S.C. 154(b) by 590 days.

(21) Appl. No.: 12/541,584

(22) Filed: Aug. 14, 2009

(65) Prior Publication Data

US 2010/0056474 A1    Mar. 4, 2010

Related U.S. Application Data

(60) Provisional application No. 61/189,149, filed on Aug. 16, 2008, provisional application No. 61/158,328, filed on Mar. 6, 2009.

(51) Int. Cl.
*A61K 31/722*   (2006.01)

(52) U.S. Cl.
CPC .................................. *A61K 31/722* (2013.01)

(58) Field of Classification Search
CPC .................................................. A61K 31/722
See application file for complete search history.

(56) References Cited

U.S. PATENT DOCUMENTS

| | | | |
|---|---|---|---|
| 2003/0162838 A1* | 8/2003 | Yumioka et al. ............. | 514/625 |
| 2007/0281904 A1 | 12/2007 | Baker et al. | |
| 2009/0117213 A1 | 5/2009 | Beaulieu et al. | |
| 2009/0166916 A1 | 7/2009 | Chou et al. | |

FOREIGN PATENT DOCUMENTS

| | | |
|---|---|---|
| WO | 02/15698 | 2/2002 |
| WO | 2007/142609 | 12/2007 |

OTHER PUBLICATIONS

Encyclopedia of Polymer Science and Technology, "Degree of Substitution"; Jan. 2011, 2 pages.*
Hu, Y. et al., Carbohydrate Polymers, "Synthesis, characterization and antibacterial activity of guanidinylated chitosan", 2007 (published online Jun. 2006), vol. 67, pp. 66-72.*
Jeon, Y.-J. et al., Journal of Microbiology and Biotechnology, "Effect of Antimicrobial Activity by Chitosan Oligosaccharide N-Conjugated with Asparagine", 2001, vol. 11, No. 2, pp. 281-286.*
International Search Report and Written Opinion in corresponding International Application PCT/US2009/053867, 10 pgs., dated Dec. 4, 2010.
Rabea et al., "Chitosan as antimicrobial agent: applications and mode of action", Biomacromolecules, ACS, Washington, DC, vol. 4, No. 6, p. 1457-1465 (Sep. 3, 2003).
Yu et al., "Cytocompatibility and antibacterial activity of a PHBV membrane with surface-immobilized water-soluble chitosan and chondroitin-6-sulfate", Macromolecular Bioscience, vol. 6, No. 5 (May 23, 2006).
Hu, et al., "Synthesis, charaterization and antibacterial activity of guanidinylated chitosan" Carbohydrate Polymers, vol. 67, pp. 66-72 (2007).
Labandiera-Rey et al., "*Staphylococcus aureus* Panton-Valentine Leukocidin Causes Necrotizing Pneumonia," 315 Science, 1130 (2007).
Miller et al., "Necrotizing Fasciitis Caused by Community-Associated Methicillin-Resistant *Staphylococcus aureus* in Los Angeles," *Staphylococcus aureus* Disease? 352 New England J. of Med., 1445, No. 14 (2005).
Said-Salim et al., "Differential Distribution And Expression of Panton-Valentine Leucocidin Among Community-Acquired Methicillin-Resistant *Staphylococcus aureus* Strains," 43 J. Clin. Microbiol, 3373 (2005).
Voyich et al., Is Panton-Valentine Leukocidin The Major Virulence Determinant In Community-Associated Methicillin-resistant 194 J. Infect. Dis., 1761 (2006).

* cited by examiner

*Primary Examiner* — Shaojia Anna Jiang
*Assistant Examiner* — Bahar Craigo
(74) *Attorney, Agent, or Firm* — Lando & Anastasi LLP

(57) ABSTRACT

The present invention is directed to the treatment and prevention of nosocomial infections or MRSA infections utilizing soluble chitosan or chitosan derivative compounds. These chitosan-derivative compounds, e.g., chitosan-arginine and chitosan-acid amines, exhibit bactericidal activity against bacterial pathogens, e.g., drug resistant bacteria such as Methicillin-resistant *Staphylococcus aureus* (MRSA).

19 Claims, 24 Drawing Sheets

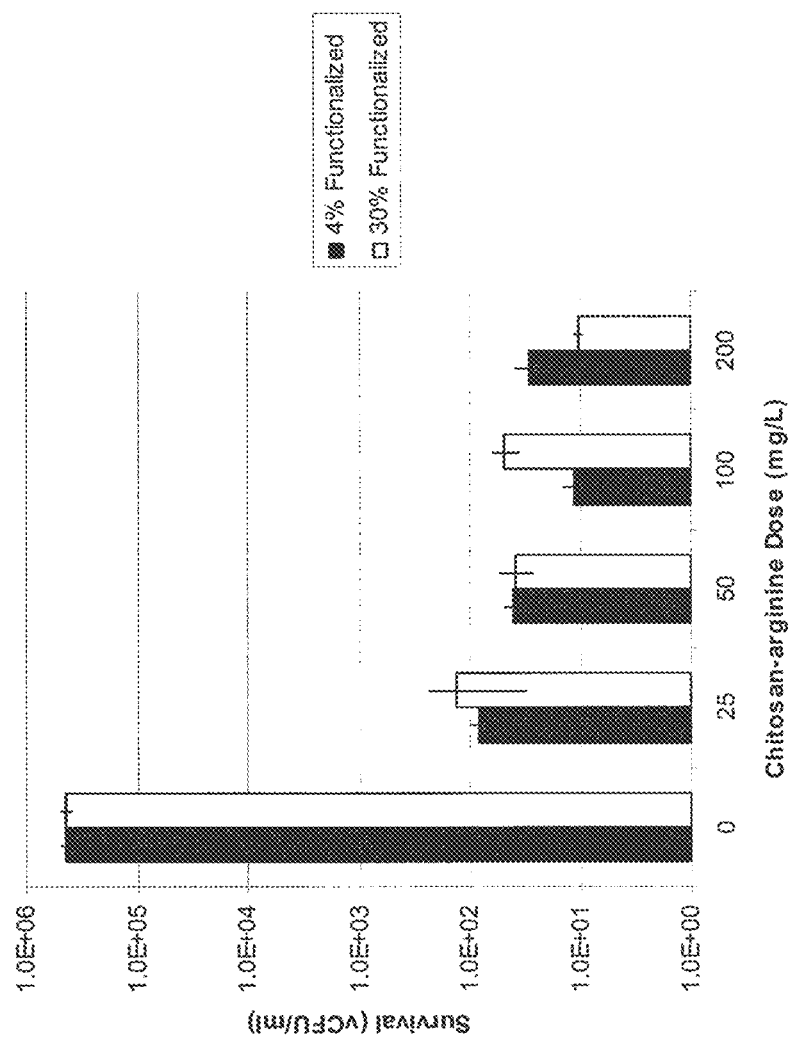

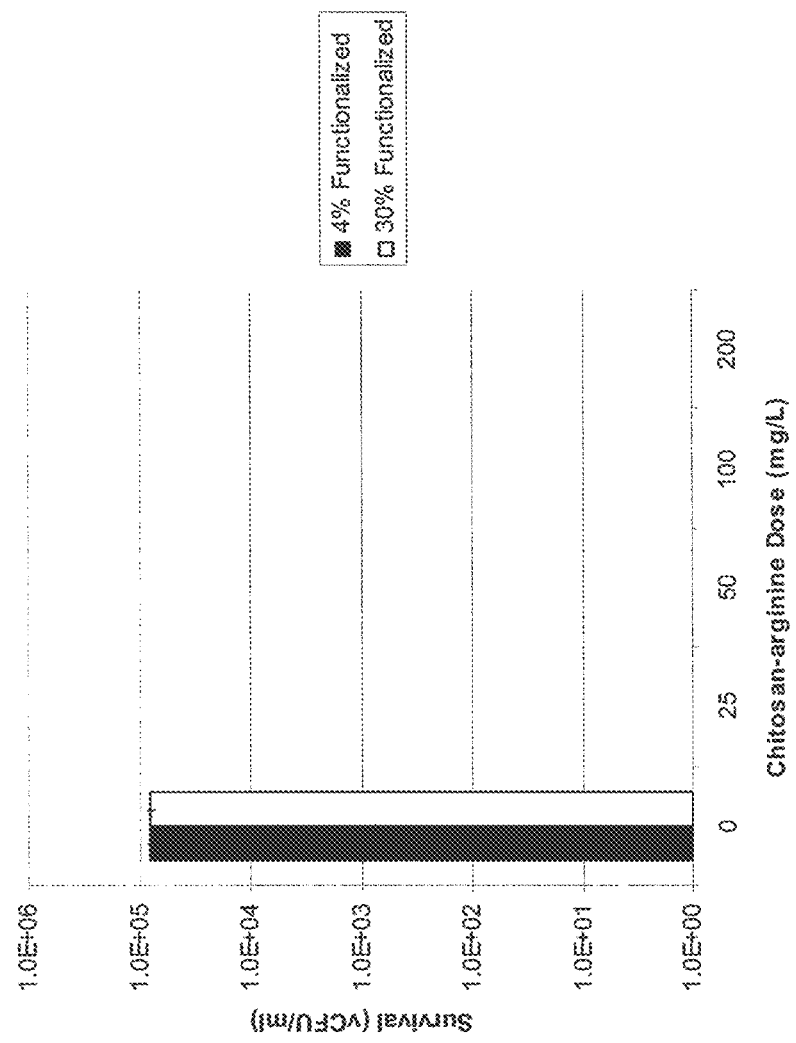

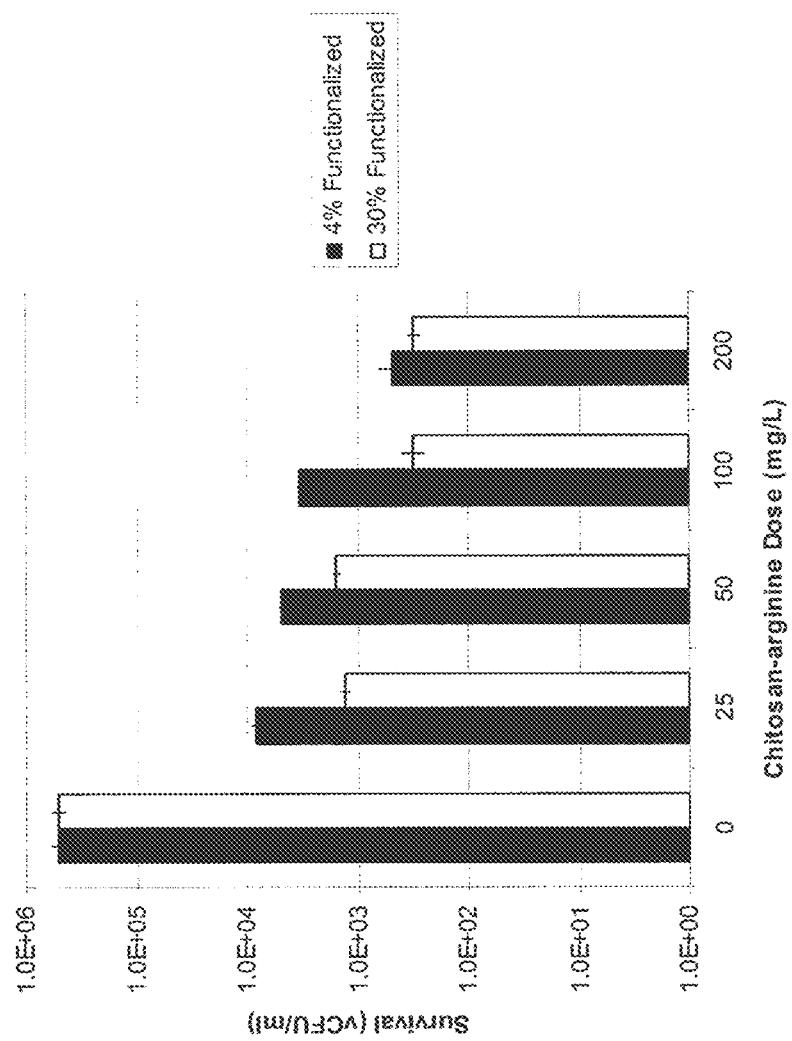

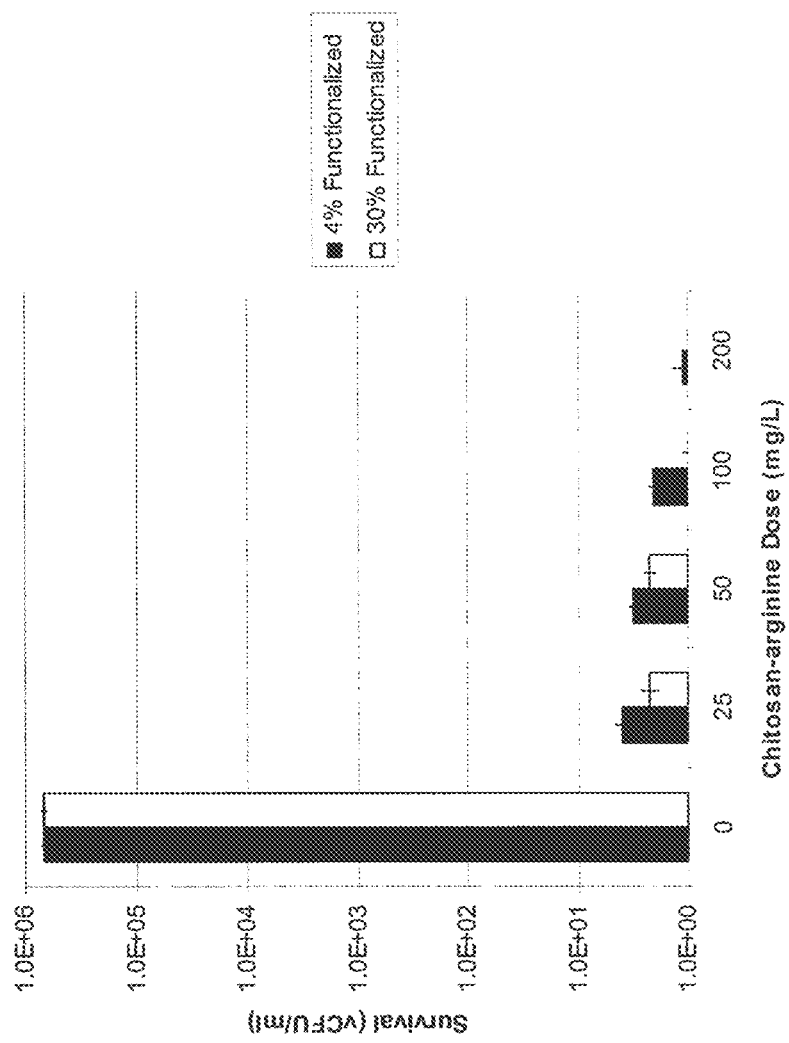

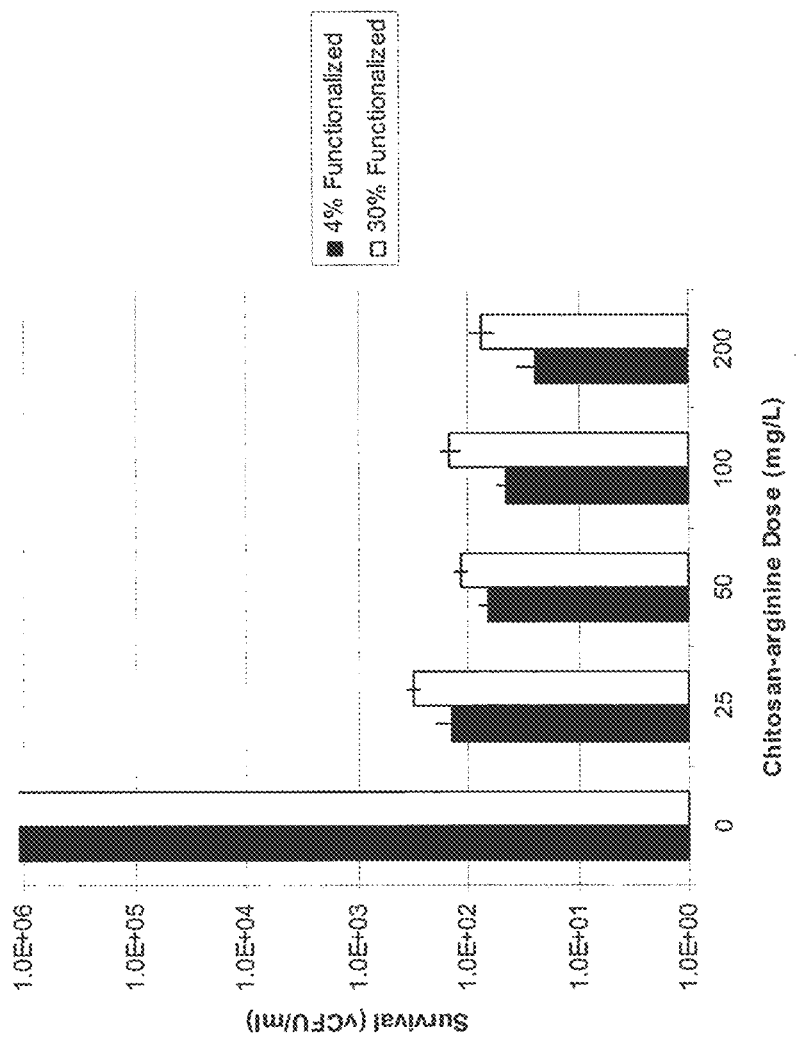

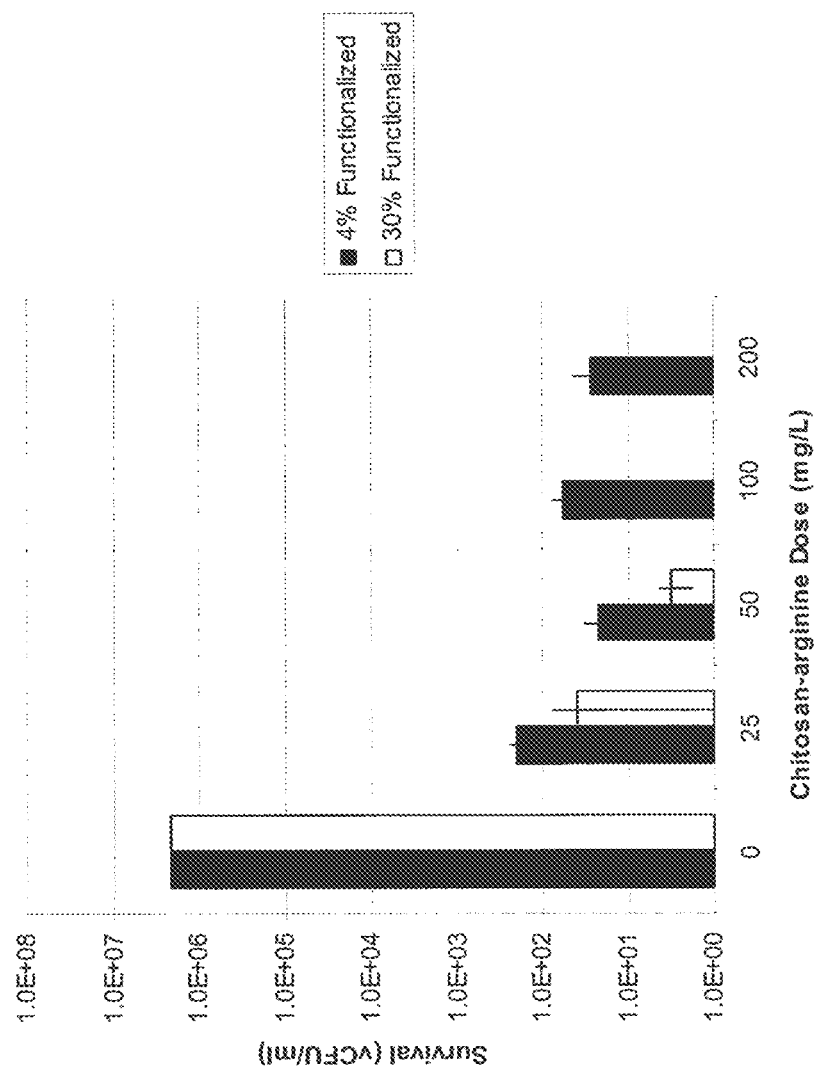

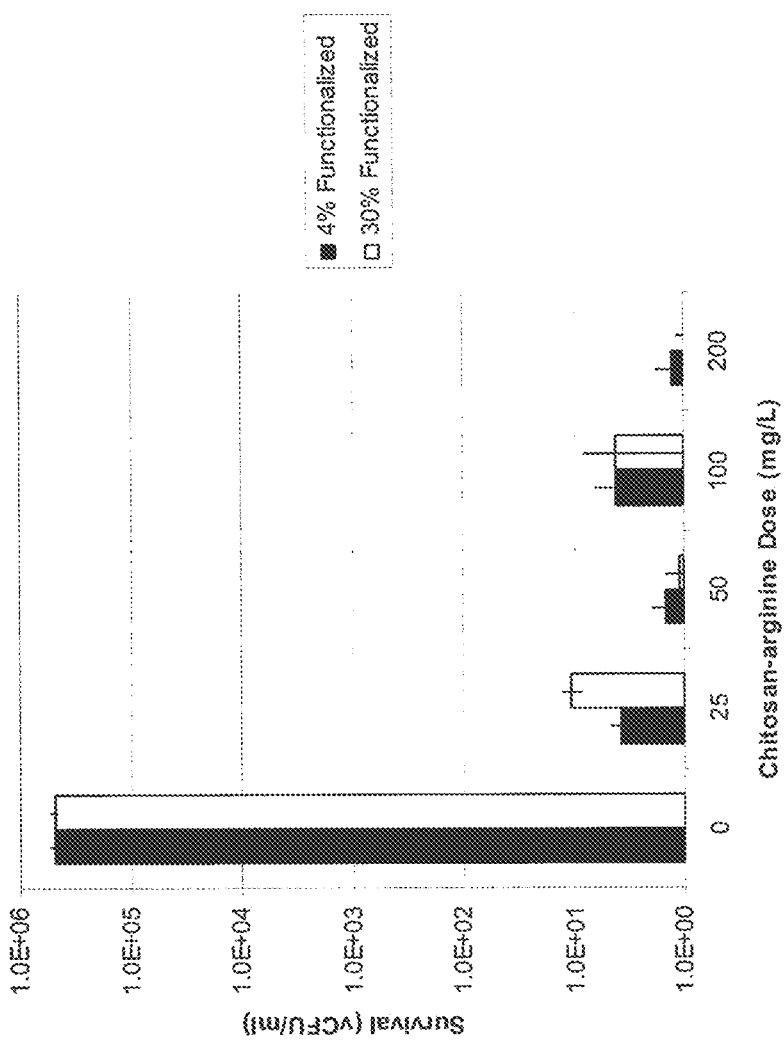

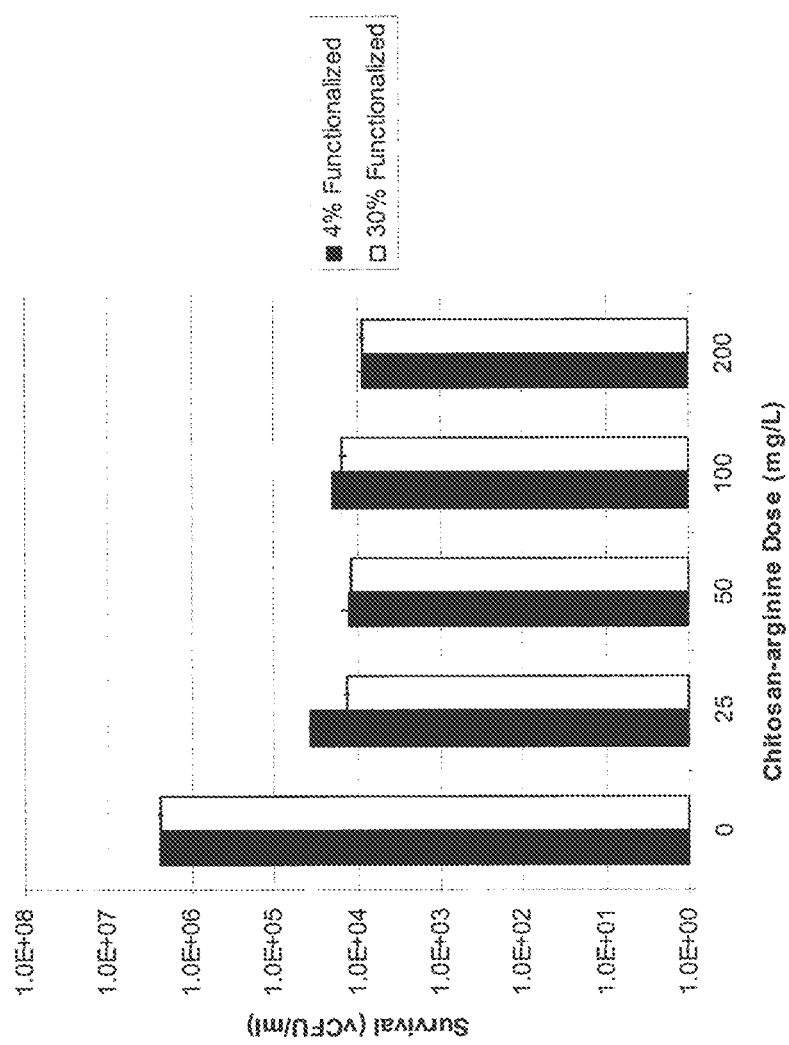

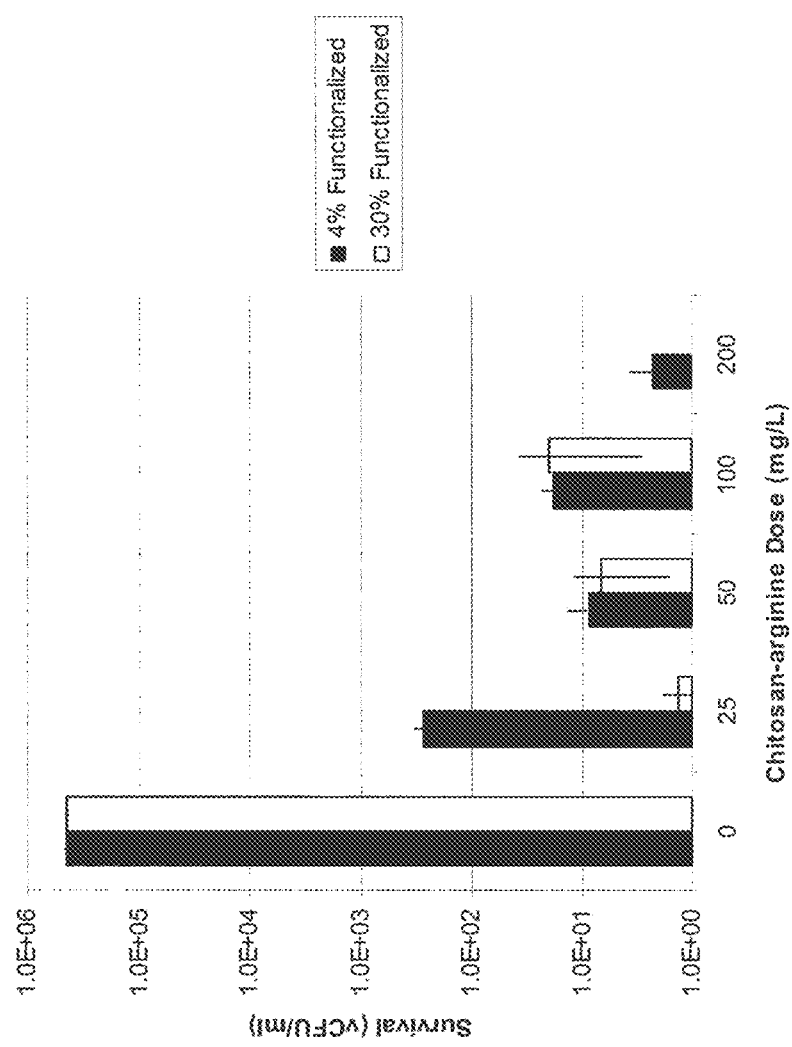

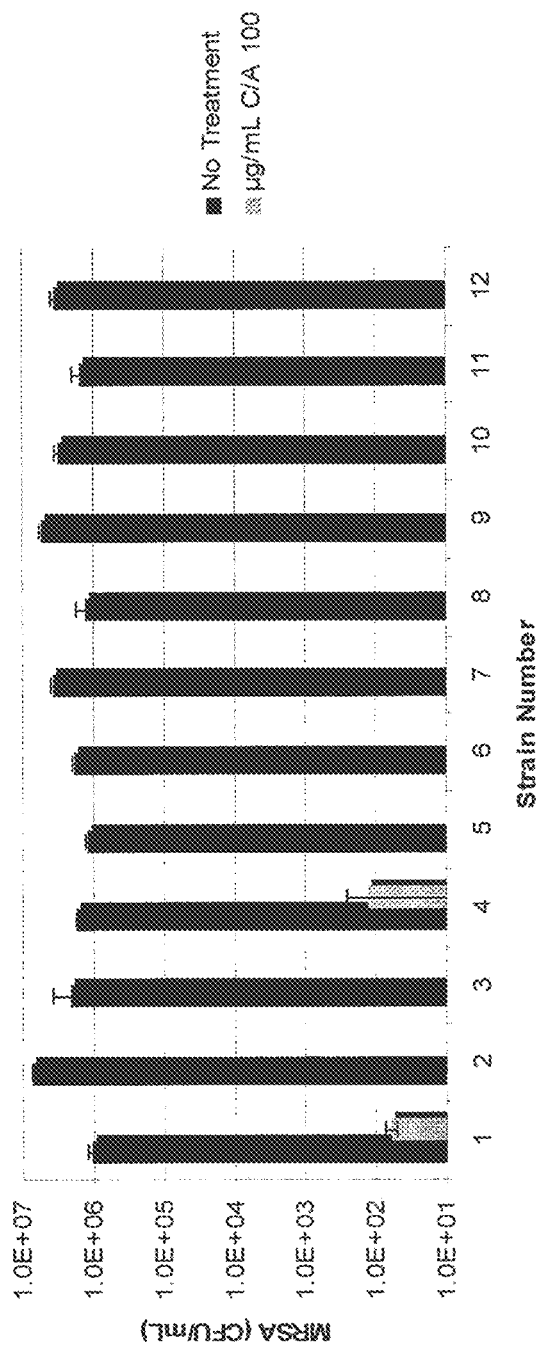

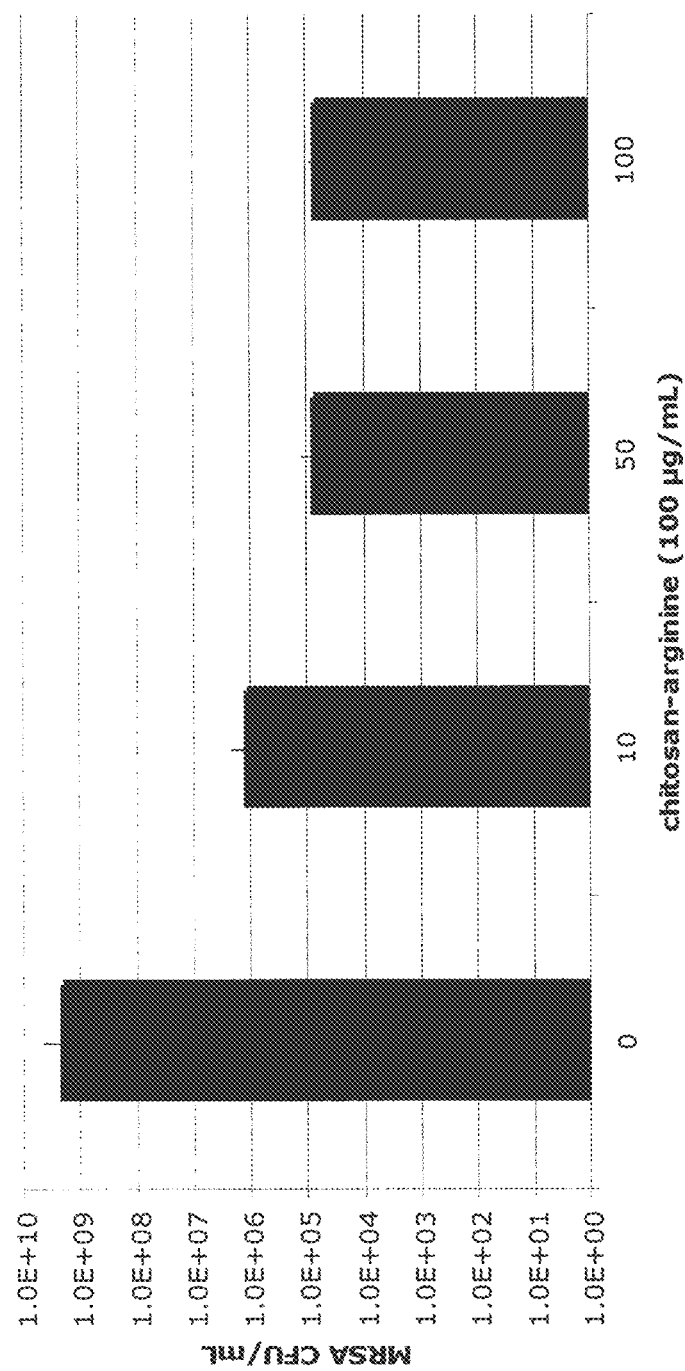

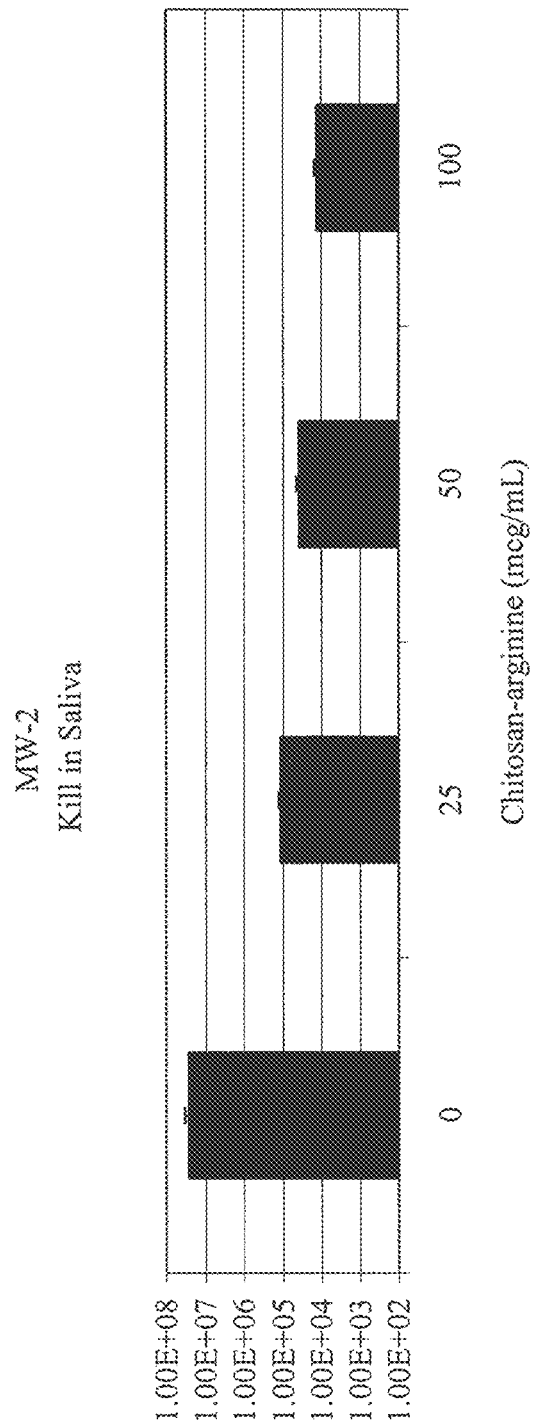

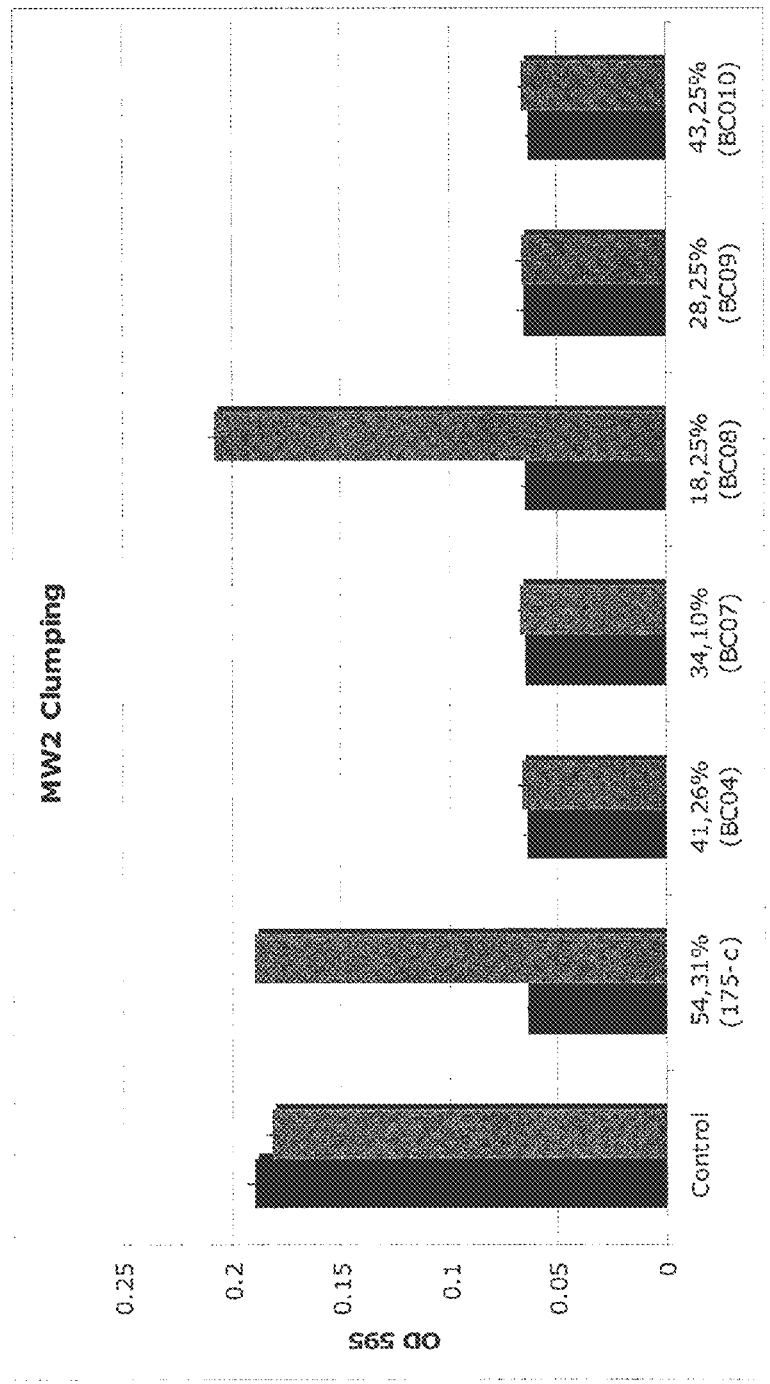

METHODS AND COMPOSITIONS FOR THE PREVENTION OF AND TREATMENT OF INFECTIONS UTILIZING CHITOSAN-DERIVATIVE COMPOUNDS

CROSS REFERENCE TO RELATED APPLICATIONS

This application claims priority to U.S. Ser. No. 61/189,149 filed on Aug. 16, 2008, and U.S. Ser. No. 61/158,328 filed on Mar. 6, 2009. The contents of the aforementioned applications are hereby incorporated by reference in their entirety.

GOVERNMENT SUPPORT

As outlined under 37 CFR 401.14(b), the United States government shall have a nonexclusive, nontransferable, irrevocable, paid-up license to practice or have practiced for or on behalf of the United States the subject invention.

FIELD OF THE INVENTION

The invention relates to soluble chitosan and derivatized chitosan and their use to treat bacterial infections, e.g., nosocomial infections or MRSA infections.

BACKGROUND

The prevalence and virility of nosocomial infections, coupled with the growing threat of antibiotic resistance and side effects of certain medications, highlight the urgent need for improved methods to safely and effectively prevent increasingly common multi-drug resistant infections. Medical facilities have reported increasing rates of nosocomial infections with major complications of burn injuries due to bacterial infections. Likewise, rising multi-drug resistance increases the risk and magnitude of infection in traumatic and surgical wounds. In the civilian setting in 2007, approximately 1.7 million people acquire a nosocomial infection while hospitalized, resulting in nearly 100,000 deaths annually. The majority of these infections are attributed to methicillin-resistant *Staphylococcus aureus* (MRSA). While hospitals have instituted improved hygiene habits for caregivers as well as MRSA admission screening protocols, these implementations have not effectively served to reduce the spread of nosocomial MRSA. In addition to the hospital environment, the close quarters of prisons and daycare centers may also facilitate elevated rates of nosocomial infections. The need for safe, prophylactic infection prevention is imperative to help control nosocomial infections and save lives. A rapid, cost-effective and nontoxic method of decontamination offers the greatest potential to reduce nosocomial infection. The Food and Drug Administration has recognized the bactericidal activity of chitosan. Research by our group has demonstrated an extremely broad-spectrum antimicrobial capability of chitosan-based materials, which indicates the potential to create non-toxic, efficacious, wide-ranging technologies to kill multi-drug resistant microorganisms in a variety of applications. Of key importance, because they are a fibrous polysaccharide that is not absorbed or metabolized by the body, these chitosan-based products are biocompatible.

Chitosan, a biopolymer derived from the second most abundant polymer on earth, chitin, has been widely used as a hemostatic bandage, cellular scaffold, and dietary supplement because it is biocompatible, biodegradable, and non-toxic. Chitosan has also shown antibacterial properties only present when dissolved in aqueous acidic solutions. In acid, the chitosan become polycationic, a property associated both with its solubility in acid as well as its antibacterial properties. We have developed chitosan based derivatives that readily dissolve in neutral water or saline which demonstrate enhanced antibacterial properties while maintaining the desirable characteristics of chitosan mentioned previously. These compounds will not require the area to be sealed during treatment and pose no threat to human health or the environment. In addition, the material can be stored as a dry powder or dissolved in water, saline, or other neutral solution with a long shelf life and dispersed when needed.

Multi-drug resistant *Enterococci*, *Staphylococci* and *Pneumococci* have become common nosocomial pathogens. These drug resistant organisms have been rapidly spreading by horizontal transfer of resistance elements and clonal spread through the medical system. Because these resistant organisms also form intractable biofilms on tissue and medical devices, deaths from these infections have been rising throughout the past two decades. More recently, community acquired methicillin resistant *Staphylococcus aureus* (CA-MRSA) have been associated with increasingly virulent infections, including toxic shock syndrome (TSS), purpura fulminans and necrotizing fasciitis. Recent work with CA-MRSA strains has implicated Panton-Valentin leukocidin (PVL) as a major virulence determinant. See M. Labandiera-Rey et al., "*Staphylococcus Aureus* Panton-Valentine Leukocidin Causes Necrotizing Pneumonia," 315 Science, 1130 (2007); B. Said-Salim et al., "Differential Distribution And Expression of Panton-Valentine Leucocidin Among Community-Acquired Methicillin-Resistant *Staphylococcus Aureus* Strains," 43 J. Clin. Microbiol, 3373 (2005); J. Voyich et al., "Is Panton-Valentine Leukocidin The Major Virulence Determinant In Community-Associated Methicillin-resistant *Staphylococcus Aureus* Disease?" 194 J. Infect. Dis., 1761 (2006); and Loren G. Miller et al., "Necrotizing Fasciitis Caused by Community-Associated Methicillin-Resistant *Staphylococcus Aureus* in Los Angeles," 352 New England J. of Med., 1445, No. 14 (2005). Additionally, because of the rapid onset of these toxicoses, the use of traditional systemic antibiotics is frequently unhelpful.

Chitosan and chitosan derivative compounds demonstrate effective treatment of MRSA. Because chitosan is biodegradable, non-toxic and exhibits antibacterial activity against a broad spectrum of microorganisms, it has been utilized in the medical arena. However, the use of chitosan is limited because of its insolubility at neutral and physiological pH.

SUMMARY OF THE INVENTION

Methods to treat or prevent bacterial infection, e.g., nosocomial infections or MRSA infections using soluble chitosans or derivatized chitosans are described herein.

It is an objective of the present invention to provide a biocompatible soluble chitosanchitosan-derivative compound that is exhibit broad spectrum antimicrobial abilities.

It is an objective of the present invention to provide a chitosan derivative compound that is shelf-stable in dry powder form or dissolve in water, saline, or other neutral solution and dispersed as needed.

It is also an objective of the present invention to provide a soluble chitosan or chitosan-derivative compound that is capable of treating nosocomial infections or MRSA infection.

It is also an objective of the present invention to provide a chitosan-derivative compound that is capable of preventing the spread of nosocomial infections or MRSA infection.

It is also an objective of the present invention to provide a chitosan-derivative compound that is effective at preventing growth of MRSA on surfaces.

It is also an objective of the present invention to provide a chitosan-derivative compound that shows potent efficacy as a bactericidal in multiple *Staphylococcus aureus* strains.

It is also an objective of the present invention to provide a chitosan-derivative compound that is capable of controlling the growth of MRSA by clumping.

These and other objectives are described herein.

In one aspect, the invention features a method of treating or preventing a nosocomial infection (or disorder), *Staphylococcus* infection (or disorder), or methicillin-resistant *Staphylococcus aureus* (MRSA) infection (or disorder), reducing or preventing the spread of nosocomial infection, *Staphylococcus* infection (or disorder), or MRSA infection, reducing *Staphylococcus* or MRSA load, or treating or preventing a symptom of nosocomial infection, *Staphylococcus* infection (or disorder), or MRSA infection, the method comprises:

administering, to a subject who has nosocomial infection, *Staphylococcus* infection (or disorder), or MRSA infection, or a symptom of nosocomial infection, *Staphylococcus* infection (or disorder), or MRSA infection, or is at risk of nosocomial infection, *Staphylococcus* infection, or MRSA infection, an effective amount of soluble chitosan or derivatized chitosan, thereby treating or preventing the nosocomial infection (or disorder), *Staphylococcus* infection (or disorder), or MRSA infection (or disorder), reducing or preventing the spread of nosocomial infection, *Staphylococcus* infection, or MRSA infection, reducing *Staphylococcus* or MRSA load, or treating or preventing the symptom of nosocomial infection, *Staphylococcus* infection, or MRSA infection.

In some embodiments, the soluble chitosan or derivatized chitosan is administered to treat nosocomial infection (or disorder).

In some embodiments, the soluble chitosan or derivatized chitosan is administered to treat *Staphylococcus* infection (or disorder).

In some embodiments, the soluble chitosan or derivatized chitosan is administered to treat MRSA infection (or disorder).

In some embodiments, the soluble chitosan or derivatized chitosan is administered to prevent nosocomial infection (or disorder).

In some embodiments, the soluble chitosan or derivatized chitosan is administered to prevent *Staphylococcus* infection (or disorder).

In some embodiments, the soluble chitosan or derivatized chitosan is administered to prevent MRSA infection (or disorder).

In some embodiments, the soluble chitosan or derivatized chitosan is administered to reduce the spread of nosocomial infection.

In some embodiments, the soluble chitosan or derivatized chitosan is administered to prevent the spread of nosocomial infection.

In some embodiments, the soluble chitosan or derivatized chitosan is administered to reduce the spread of *Staphylococcus* infection (or disorder).

In some embodiments, the soluble chitosan or derivatized chitosan is administered to prevent the spread of *Staphylococcus* infection (or disorder).

In some embodiments, the soluble chitosan or derivatized chitosan is administered to reduce the spread of MRSA infection.

In some embodiments, the soluble chitosan or derivatized chitosan is administered to prevent the spread of MRSA infection.

In some embodiments, the soluble chitosan or derivatized chitosan is administered to reduce *Staphylococcus* load in the subject.

In some embodiments, the soluble chitosan or derivatized chitosan is administered to reduce MRSA load in the subject.

In some embodiments, the soluble chitosan or derivatized chitosan is administered to treat a symptom of nosocomial infection.

In some embodiments, the soluble chitosan or derivatized chitosan is administered to prevent a symptom of nosocomial infection.

In some embodiments, the soluble chitosan or derivatized chitosan is administered to treat a symptom of *Staphylococcus* infection.

In some embodiments, the soluble chitosan or derivatized chitosan is administered to prevent a symptom of *Staphylococcus* infection.

In some embodiments, the soluble chitosan or derivatized chitosan is administered to treat a symptom of MRSA infection.

In some embodiments, the soluble chitosan or derivatized chitosan is administered to prevent a symptom of MRSA infection.

In some embodiments, the subject is a human or an animal, e.g., a horse or a cow.

In some embodiments, the nosocomial infection, *Staphylococcus* infection, or MRSA infection (or disorder) has previously been treated with an antibiotic without a soluble chitosan or derivatized chitosan, e.g., said treatment was unsatisfactory.

In some embodiments, the subject has one or more symptoms selected from a group consisting of: a red, swollen and painful area on the skin, drainage of pus or other fluids from the infected site, fever, skin abscess, warmth around the infected area, chest pain, chills, fatigue, fever, malaise, headache, muscle aches, rash, wound, skin breach, and/or shortness of breath.

In some embodiments, the subject is at risk for nosocomial infection (disorder) or MRSA infection (or disorder), e.g., a person with weak immune system (e.g., an AIDS patient, a cancer patient, or a severe asthmatic), a diabetic, a cystic fibrosis patient, an athlete participating in contact sports or weight training, a young children, an elderly, a person staying in a health care facility for an extended period of time, a person living in confined space with other people, a person using an invasive devise (e.g., a person who is on dialysis, is catheterized, or has feeding tubes), a person who has recent antibiotic use (e.g., treatment with fluoroquinolones (Ciprofloxacin, Ofloxacin or Levofloxacin) or cephalosporin antibiotics in the past four weeks), or a surfer who spend large amounts of time in coast waters where MRSA is present.

In some embodiments, the soluble chitosan or derivatized chitosan is administered topically, enterally or parenterally.

In some embodiments, the soluble chitosan or derivatized chitosan is administered by inhalation (e.g., nasal) spray.

In some embodiments, the effective amount is therapeutically effective amount.

In some embodiments, the soluble chitosan or derivatized chitosan is not administered in combination with a second therapy, e.g., an antibiotic, (e.g., Clindamycin, Linezolid, Tetracycline, Trimethoprim-sulfamethoxazole, or Vancomycin).

In some embodiments, the MRSA is selected from EMRSA15 strain, EMRSA16 strain (ST36:USA200 or MRSA252), CC8 strain designated ST8:USA300, ST8: USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the bacterium is selected from other *Staphylococcus* species such as *S. aureus, S. epidermidis, S. staprophyticus, S. lugdunensis, S. schleiferi,* and *S. caprae* and their drug resistant strains, clinical isolates from a hospital, and/or other *Staphylococcus* strains described herein.

In some embodiments, the soluble chitosan or derivatized chitosan reduces the chance of *Staphylococcus* spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces *Staphylococcus* load in the subject by at least 10, 20, 30, 40, 50, 60, 70, 80, 90, 95, 99, 99.9, or 99.99%, compared to the *Staphylococcus* load in the subject before treatment with the soluble chitosan or derivatized chitosan.

In some embodiments, the soluble chitosan or derivatized chitosan reduces the chance of MRSA spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces MRSA load in the subject by at least 10, 20, 30, 40, 50, 60, 70, 80, 90, 95, 99, 99.9, or 99.99%, compared to the MRSA load in the subject before treatment with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

formula (I)

[chemical structure of chitosan polymer with OH, HO, NH-R¹ groups and n repeat units]

wherein:
n is an integer between 20 and 6000; and
each $R^1$ is independently selected for each occurrence from hydrogen, acetyl, and a group of formula (II):

formula (II)

[chemical structure showing O=C-CH(R²)(R³)]

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

[two chemical structures of arginine-derived side chains with NH₂ and guanidino groups] and In some embodiments, $R^2$ is amino and $R^3$ is a lysine side chain.

In some embodiments, $R^1$ is selected from one of the following:

[two chemical structures of lysine-derived side chains with NH₂ groups] and

In some embodiments, $R^2$ is amino and $R^3$ is a histidine side chain.

In some embodiments, $R^1$ is selected from one of the following:

[two chemical structures of histidine-derived side chains with imidazole rings] and In some embodiments, at least 1% of $R^1$ substituents are selected from one of the following:

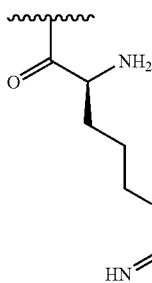 and 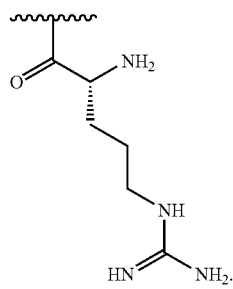

AND at least 1% of $R^1$ substituents are selected from the following:

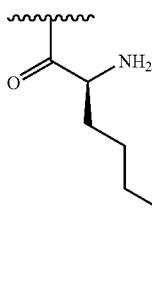 and 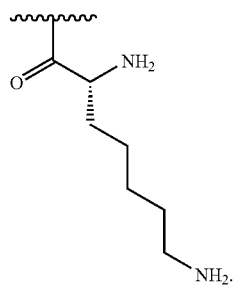.

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

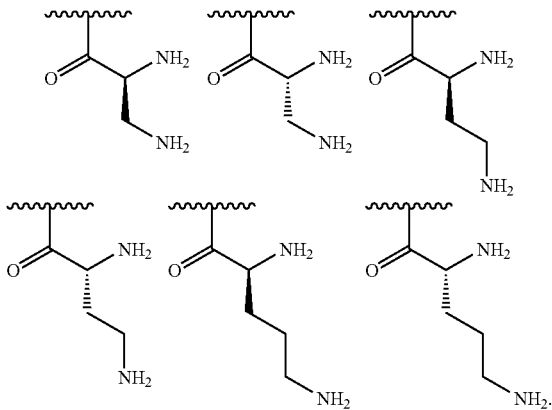

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

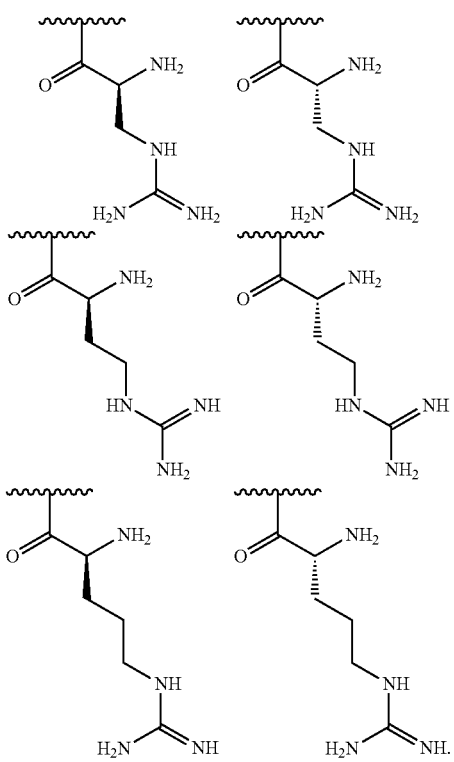

In some embodiments, $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

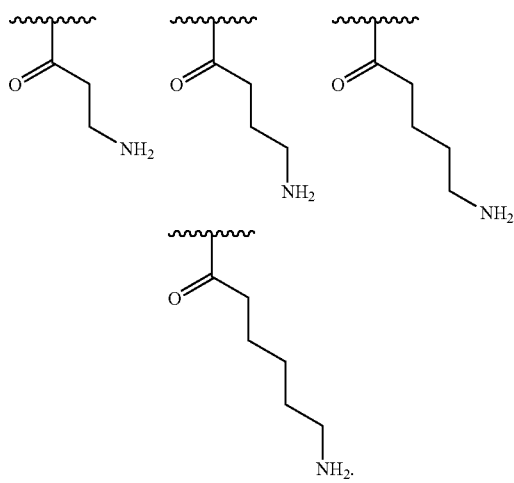

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

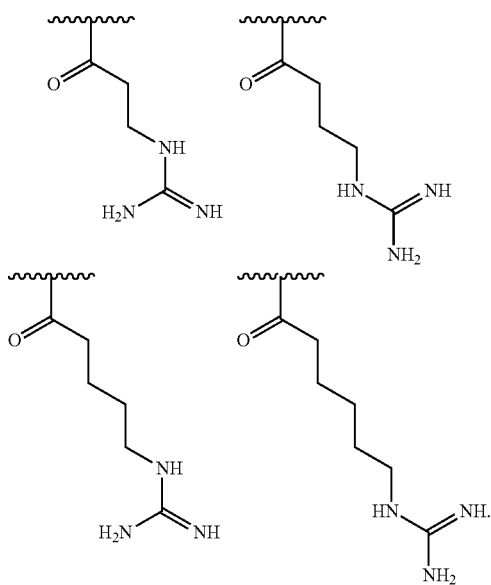

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

In another aspect, the invention features a pharmaceutical composition for treating and preventing a nosocomial infection (or disorder), *Staphylococcus* infection (or disorder), or MRSA infection (or disorder), reducing or preventing the spread of a nosocomial infection, *Staphylococcus* infection, or MRSA infection, reducing, *Staphylococcus* or MRSA load, or treating or preventing a symptom of a nosocomial infection, *Staphylococcus* infection, or MRSA infection in a subject, wherein the composition comprises a soluble chitosan or derivatized chitosan described herein.

In some embodiments, the soluble chitosan or derivatized chitosan is administered to treat nosocomial infection (or disorder).

In some embodiments, the soluble chitosan or derivatized chitosan is administered to treat *Staphylococcus* infection (or disorder).

In some embodiments, the soluble chitosan or derivatized chitosan is administered to treat MRSA infection (or disorder).

In some embodiments, the soluble chitosan or derivatized chitosan is administered to prevent nosocomial infection (or disorder).

In some embodiments, the soluble chitosan or derivatized chitosan is administered to prevent *Staphylococcus* infection (or disorder).

In some embodiments, the soluble chitosan or derivatized chitosan is administered to prevent MRSA infection (or disorder).

In some embodiments, the soluble chitosan or derivatized chitosan is administered to reduce the spread of nosocomial infection.

In some embodiments, the soluble chitosan or derivatized chitosan is administered to prevent the spread of nosocomial infection.

In some embodiments, the soluble chitosan or derivatized chitosan is administered to reduce the spread of *Staphylococcus* infection.

In some embodiments, the soluble chitosan or derivatized chitosan is administered to prevent the spread of *Staphylococcus* infection.

In some embodiments, the soluble chitosan or derivatized chitosan is administered to reduce the spread of MRSA infection.

In some embodiments, the soluble chitosan or derivatized chitosan is administered to prevent the spread of MRSA infection.

In some embodiments, the soluble chitosan or derivatized chitosan is administered to reduce *Staphylococcus* load in the subject.

In some embodiments, the soluble chitosan or derivatized chitosan is administered to reduce MRSA load in the subject.

In some embodiments, the soluble chitosan or derivatized chitosan is administered to treat a symptom of nosocomial infection.

In some embodiments, the soluble chitosan or derivatized chitosan is administered to prevent a symptom of nosocomial infection.

In some embodiments, the soluble chitosan or derivatized chitosan is administered to treat a symptom of *Staphylococcus* infection.

In some embodiments, the soluble chitosan or derivatized chitosan is administered to prevent a symptom of *Staphylococcus* infection.

In some embodiments, the soluble chitosan or derivatized chitosan is administered to treat a symptom of MRSA infection.

In some embodiments, the soluble chitosan or derivatized chitosan is administered to prevent a symptom of MRSA infection.

In some embodiments, the subject is a human or an animal, e.g., a horse or a cow.

In some embodiments, the nosocomial infection, *Staphylococcus* infection, or MRSA infection (or disorder) has previously been treated with an antibiotic without a soluble chitosan or derivatized chitosan, e.g., said treatment was unsatisfactory.

In some embodiments, the subject has one or more symptoms selected from a group consisting of: a red, swollen and painful area on the skin, drainage of pus or other fluids from the infected site, fever, skin abscess, warmth around the infected area, chest pain, chills, fatigue, fever, malaise, headache, muscle aches, rash, wound, skin breach, and/or shortness of breath.

In some embodiments, the subject is at risk for nosocomial infection (disorder), *Staphylococcus* infection (disorder), or MRSA infection (or disorder), e.g., a person with weak immune system (e.g., an AIDS patient, a cancer patient, or a severe asthmatic), a diabetic, a cystic fibrosis patient, an athlete participating in contact sports or weight training, a young children, an elderly, a person staying in a health care facility for an extended period of time, a person living in confined space with other people, a person using an invasive devise (e.g., a person who is on dialysis, is catheterized, or has feeding tubes), a person who has recent antibiotic use (e.g., treatment with fluoroquinolones (Ciprofloxacin, Ofloxacin or Levofloxacin) or cephalosporin antibiotics in the past four weeks), or a surfer who spend large amounts of time in coast waters where MRSA is present.

In some embodiments, the soluble chitosan or derivatized chitosan is administered topically, enterally or parenterally.

In some embodiments, the soluble chitosan or derivatized chitosan is administered by inhalation (e.g., nasal) spray.

In some embodiments, the effective amount is therapeutically effective amount.

In some embodiments, the soluble chitosan or derivatized chitosan is not administered in combination with a second therapy, e.g., an antibiotic, (e.g., Clindamycin, Linezolid, Tetracycline, Trimethoprim-sulfamethoxazole, or vancomycin).

In some embodiments, the MRSA is selected from EMRSA15 strain, EMRSA16 strain (ST36:USA200 or MRSA252), CC8 strain designated ST8:USA300, ST8: USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the bacterium is selected from other *Staphylococcus* species such as *S. aureus, S. epidermidis, S. staprophyticus, S. lugdunensis, S. schleiferi,* and *S. caprae* and their drug resistant strains, clinical isolates from a hospital, and/or other *Staphylococcus* strains described herein.

In some embodiments, the soluble chitosan or derivatized chitosan reduces the chance of *Staphylococcus* spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces *Staphylococcus* load in the subject by at least 10, 20, 30, 40, 50, 60, 70, 80, 90, 95, 99, 99.9, or 99.99%, compared to the *Staphylococcus* load in the subject before treatment with the soluble chitosan or derivatized chitosan.

In some embodiments, the soluble chitosan or derivatized chitosan reduces the chance of MRSA spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces MRSA load in the subject by at least 10, 20, 30, 40, 50, 60, 70, 80, 90, 95, 99, 99.9, or 99.99%, compared to the MRSA load in the subject before treatment with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

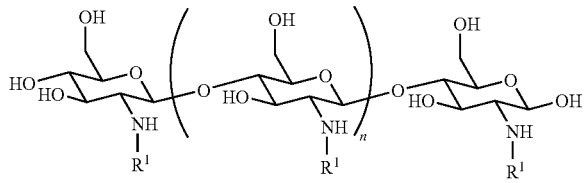

formula (I)

wherein:

n is an integer between 20 and 6000; and each $R^1$ is independently selected for each occurrence from hydrogen, acetyl, and a group of formula (II):

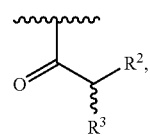

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

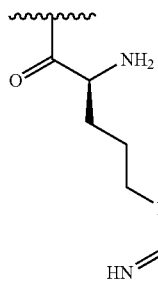 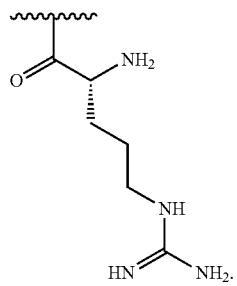

In some embodiments, $R^2$ is amino and $R^3$ is a lysine side chain.

In some embodiments, $R^1$ is selected from one of the following:

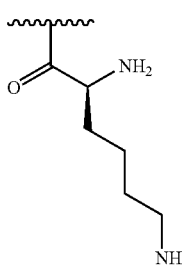 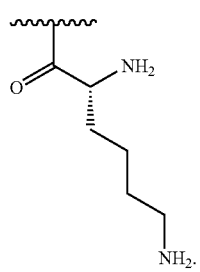

In some embodiments, $R^2$ is amino and $R^3$ is a histidine side chain.

In some embodiments, $R^1$ is selected from one of the following:

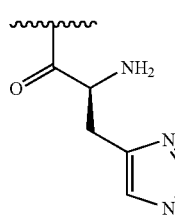 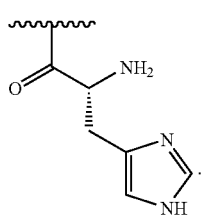

In some embodiments, at least 1% of $R^1$ substituents are selected from one of the following:

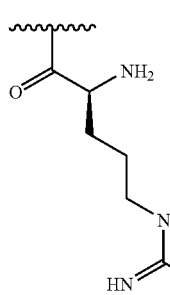 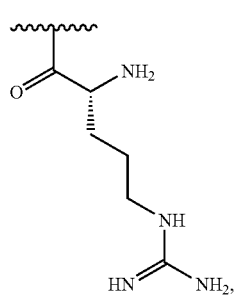

AND at least 1% of $R^1$ substituents are selected from the following:

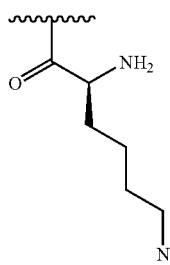 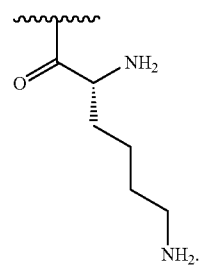

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

The composition of claim x, wherein $R^3$ is $C_2$ alkyl substituted with an amino group.

In some embodiments, $R^3$ is $C_3$ alkyl substituted with an amino group.

In some embodiments, $R^1$ is selected from one of the following:

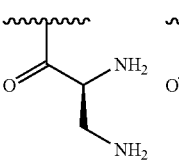 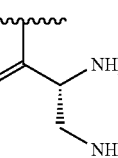 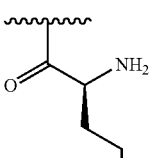

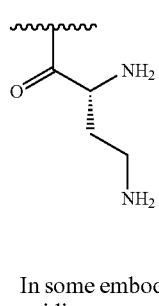 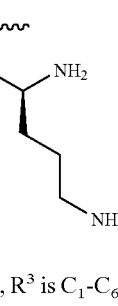 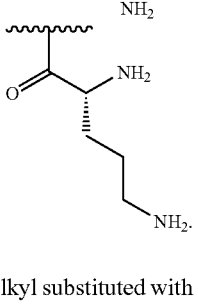

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

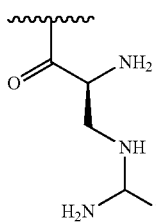 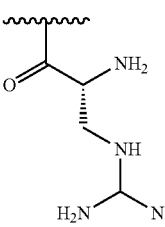

-continued

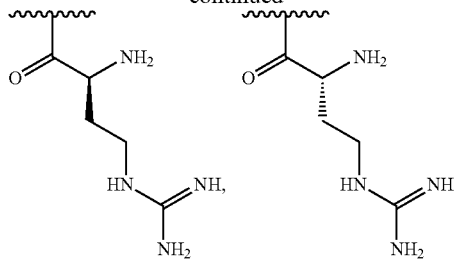

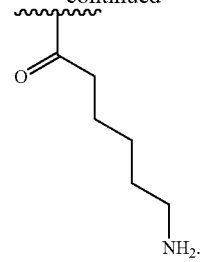

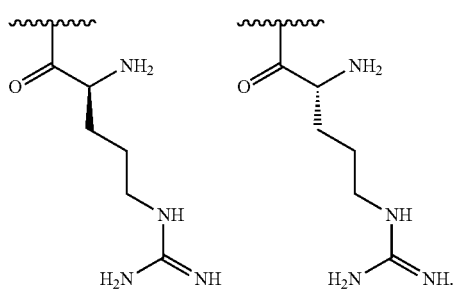

In some embodiments, $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

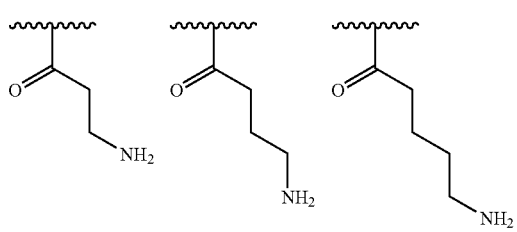

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

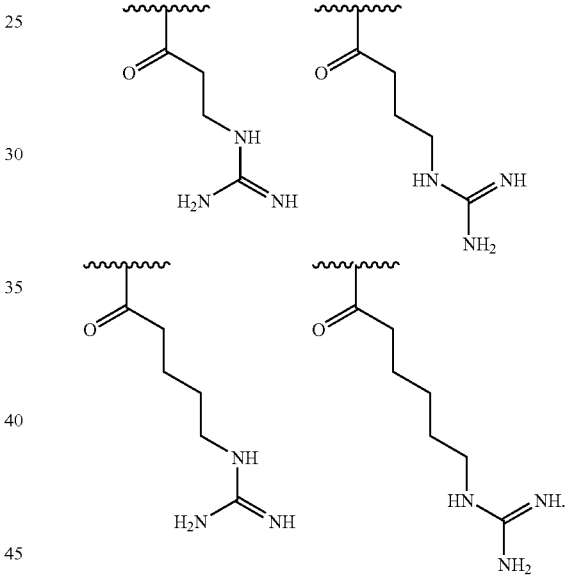

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

In yet another aspect, the invention features a kit for treating and preventing of a nosocomial infection (or disorder) or MRSA infection (or disorder), reducing or preventing the spread of a nosocomial infection or MRSA infection, reducing MRSA load, or treating or preventing a symptom of a nosocomial infection or MRSA infection in a subject, wherein the composition comprises a soluble chitosan or derivatized chitosan described herein.

In some embodiments, the soluble chitosan or derivatized chitosan is administered to treat nosocomial infection (or disorder).

In some embodiments, the soluble chitosan or derivatized chitosan is administered to treat *Staphylococcus* infection (or disorder).

In some embodiments, the soluble chitosan or derivatized chitosan is administered to treat MRSA infection (or disorder).

In some embodiments, the soluble chitosan or derivatized chitosan is administered to prevent nosocomial infection (or disorder).

In some embodiments, the soluble chitosan or derivatized chitosan is administered to prevent *Staphylococcus* infection (or disorder).

In some embodiments, the soluble chitosan or derivatized chitosan is administered to prevent MRSA infection (or disorder).

In some embodiments, the soluble chitosan or derivatized chitosan is administered to reduce the spread of nosocomial infection.

In some embodiments, the soluble chitosan or derivatized chitosan is administered to prevent the spread of nosocomial infection.

In some embodiments, the soluble chitosan or derivatized chitosan is administered to reduce the spread of *Staphylococcus* infection.

In some embodiments, the soluble chitosan or derivatized chitosan is administered to prevent the spread of *Staphylococcus* infection.

In some embodiments, the soluble chitosan or derivatized chitosan is administered to reduce the spread of MRSA infection.

In some embodiments, the soluble chitosan or derivatized chitosan is administered to prevent the spread of MRSA infection.

In some embodiments, the soluble chitosan or derivatized chitosan is administered to reduce *Staphylococcus* load in the subject.

In some embodiments, the soluble chitosan or derivatized chitosan is administered to reduce MRSA load in the subject.

In some embodiments, the soluble chitosan or derivatized chitosan is administered to treat a symptom of nosocomial infection.

In some embodiments, the soluble chitosan or derivatized chitosan is administered to prevent a symptom of nosocomial infection.

In some embodiments, the soluble chitosan or derivatized chitosan is administered to treat a symptom of *Staphylococcus* infection.

In some embodiments, the soluble chitosan or derivatized chitosan is administered to prevent a symptom of *Staphylococcus* infection.

In some embodiments, the soluble chitosan or derivatized chitosan is administered to treat a symptom of MRSA infection.

In some embodiments, the soluble chitosan or derivatized chitosan is administered to prevent a symptom of MRSA infection.

In some embodiments, the subject is a human or an animal, e.g., a horse or a sow.

In some embodiments, the nosocomial infection (or disorder), *Staphylococcus* infection (or disorder), or MRSA infection (or disorder) has previously been treated with an antibiotic without a soluble chitosan or derivatized chitosan, e.g., said treatment was unsatisfactory.

In some embodiments, the subject has one or more symptoms selected from a group consisting of: a red, swollen and painful area on the skin, drainage of pus or other fluids from the infected site, fever, skin abscess, warmth around the infected area, chest pain, chills, fatigue, fever, malaise, headache, muscle aches, rash, wound, skin breach, and/or shortness of breath.

In some embodiments, the subject is at risk for nosocomial infection (or disorder), *Staphylococcus* infection (or disorder), or MRSA infection (or disorder), e.g., a person with weak immune system (e.g., an AIDS patient, a cancer patient, or a severe asthmatic), a diabetic, a cystic fibrosis patient, an athlete participating in contact sports or weight training, a young children, an elderly, a person staying in a health care facility for an extended period of time, a person living in confined space with other people, a person using an invasive devise (e.g., a person who is on dialysis, is catheterized, or has feeding tubes), a person who has recent antibiotic use (e.g., treatment with fluoroquinolones (Ciprofloxacin, Ofloxacin or Levofloxacin) or cephalosporin antibiotics in the past four weeks), or a surfer who spend large amounts of time in coast waters where MRSA is present.

In some embodiments, the soluble chitosan or derivatized chitosan is administered topically, enterally or parenterally.

In some embodiments, the soluble chitosan or derivatized chitosan is administered by inhalation (e.g., nasal) spray.

In some embodiments, the effective amount is therapeutically effective amount.

In some embodiments, the soluble chitosan or derivatized chitosan is not administered in combination with a second therapy, e.g., an antibiotic, (e.g., Clindamycin, Linezolid, Tetracycline, Trimethoprim-sulfamethoxazole, or Vancomycin).

In some embodiments, the MRSA is selected from EMRSA15 strain, EMRSA16 strain (ST36:USA200 or MRSA252), CC8 strain designated ST8:USA300, ST8:USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the bacterium is selected from other *Staphylococcus* species such as *S. aureus, S. epidermidis, S. staprophyticus, S. lugdunensis, S. schleiferi*, and *S. caprae* and their drug resistant strains, clinical isolates from a hospital, and/or other *Staphylococcus* strains described herein.

In some embodiments, the soluble chitosan or derivatized chitosan reduces the chance of *Staphylococcus* spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces *Staphylococcus* load in the subject by at least 10, 20, 30, 40, 50, 60, 70, 80, 90, 95, 99, 99.9, or 99.99%, compared to the *Staphylococcus* load in the subject before treatment with the soluble chitosan or derivatized chitosan.

In some embodiments, the soluble chitosan or derivatized chitosan reduces the chance of MRSA spread in a subject by at least 10, 20, 30, 40, 50, 60, 70, 80, 90, 95, 99, 99.9, or 99.99%, compared to a subject who has not been treated with the soluble chitosan or derivatized chitosan.

In some embodiments, the soluble chitosan or derivatized chitosan reduces MRSA load in the subject by at least 10, 20, 30, 40, 50, 60, 70, 80, 90, 95, 99, 99.9, or 99.99%, compared to the MRSA load in the subject before treatment with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

formula (I)

wherein:

n is an integer between 20 and 6000; and each $R^1$ is independently selected for each occurrence from hydrogen, acetyl, and a group of formula (II):

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

In some embodiments, $R^2$ is amino and $R^3$ is a lysine side chain.

In some embodiments, $R^1$ is selected from one of the following:

In some embodiments, $R^2$ is amino and $R^3$ is a histidine side chain.

In some embodiments, $R^1$ is selected from one of the following:

In some embodiments, at least 1% of $R^1$ substituents are selected from one of the following:

AND at least 1% of $R^1$ substituents are selected from the following:

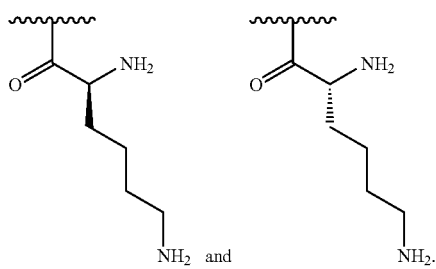 [SMILES: *C(=O)[C@@H](N)CCCCN ; "and" ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

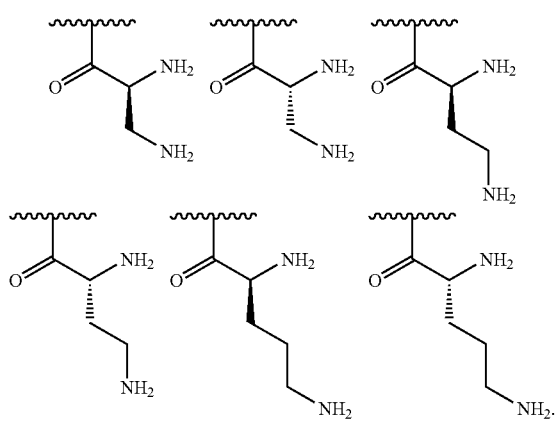

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

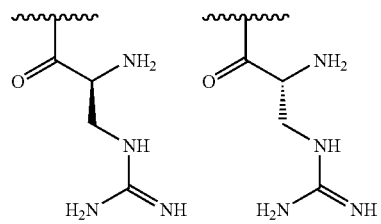

-continued

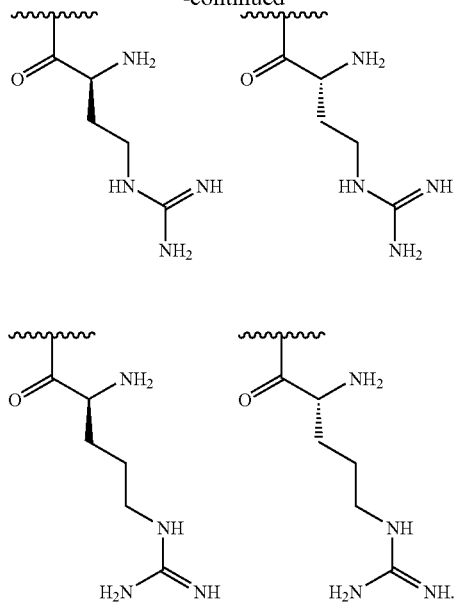

In some embodiments, $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

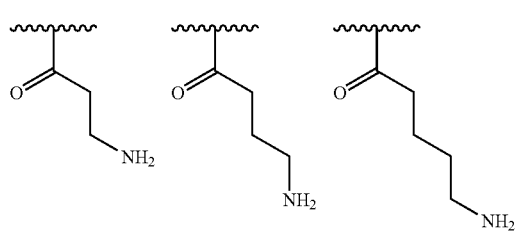

23

-continued

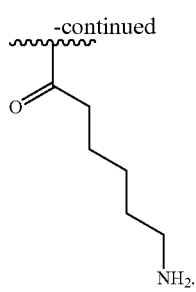

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

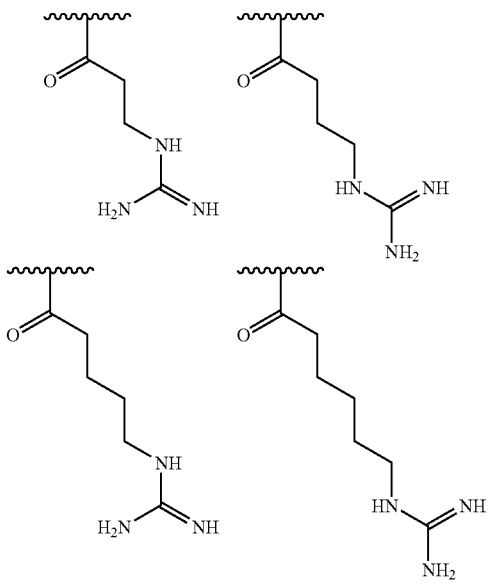

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

In one aspect, the invention features a method of inhibiting the growth (e.g., killing) of a bacterium (e.g., MRSA) in a sample, comprising contacting the sample with an effective amount of soluble chitosan or derivatized chitosan, thereby inhibiting the growth (e.g., killing) of the bacterium (e.g., MRSA) in said sample.

In some embodiments, the sample is a clinical (e.g., hospital) sample, e.g., whole blood, plasma, serum, urine, saliva, stool, sweat, tears, stool.

In some embodiments, the bacterium is a bacterium isolated from a clinical sample, e.g., a bacterium described herein.

In some embodiments, the bacterium is selected from other *Staphylococcus* species such as *S. aureus, S. epidermidis, S. staprophyticus, S. lugdunensis, S. schleiferi,* and *S. caprae* and their drug resistant strains, clinical isolates from a hospital, and/or other *Staphylococcus* strains described herein.

In some embodiments, the MRSA is selected from EMRSA15 strain, EMRSA16 strain (ST36:USA200 or MRSA252), CC8 strain designated ST8:USA300, ST8: USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the soluble chitosan or derivatized chitosan reduces the growth rate of the bacterium (e.g., MRSA) by at least 10, 20, 30, 40, 50, 60, 70, 80, 90, 95, 99, 99.9, or 99.99%, compared to a bacteria that has not been contacted with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

formula (I)

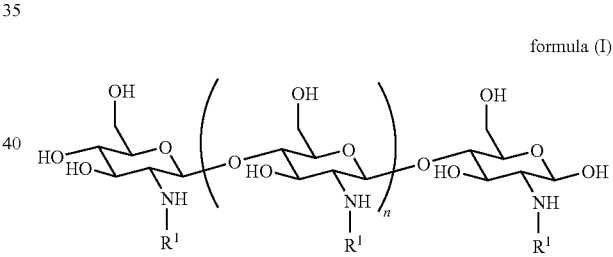

wherein:
n is an integer between 20 and 6000; and
each $R^1$ is independently selected for each occurrence from hydrogen, acetyl, and a group of formula (II):

formula (II)

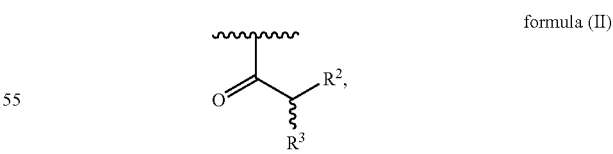

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

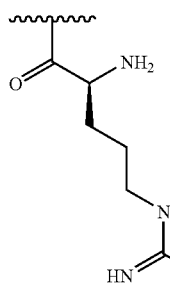 and 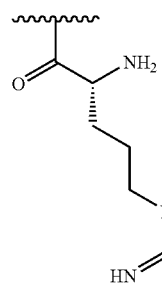

In some embodiments, $R^2$ is amino and $R^3$ is a lysine side chain.

In some embodiments, $R^1$ is selected from one of the following:

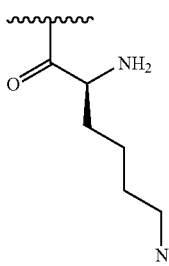 and 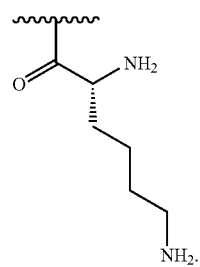

In some embodiments, $R^2$ is amino and $R^3$ is a histidine side chain.

In some embodiments, $R^1$ is selected from one of the following:

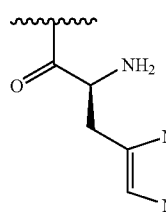 and 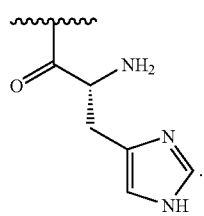

In some embodiments, at least 1% of $R^1$ substituents are selected from one of the following:

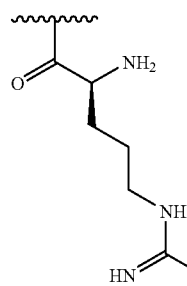 and 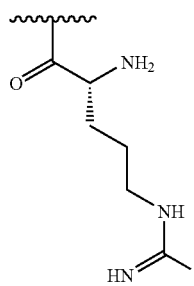,

AND at least 1% of $R^1$ substituents are selected from the following:

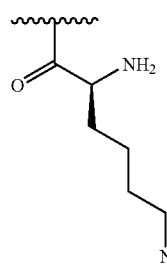 and 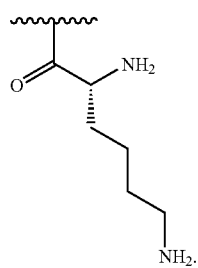.

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

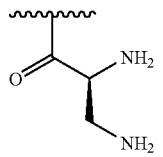 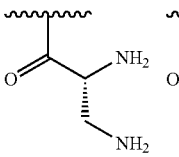 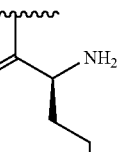

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

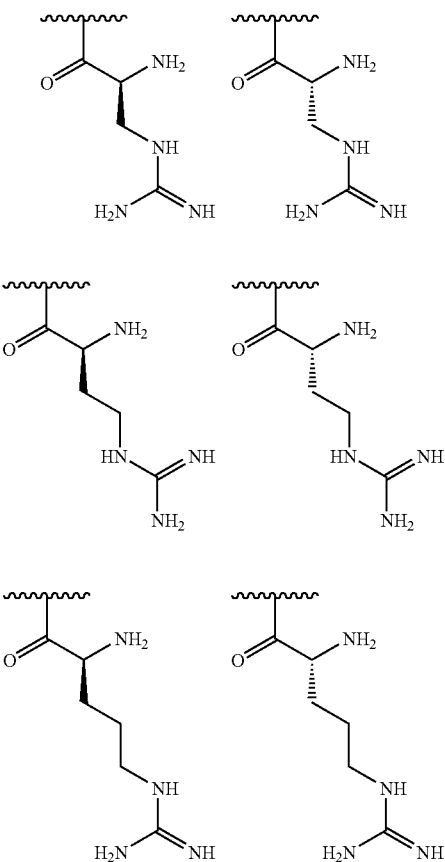

The method of any one of claims x-x, wherein $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

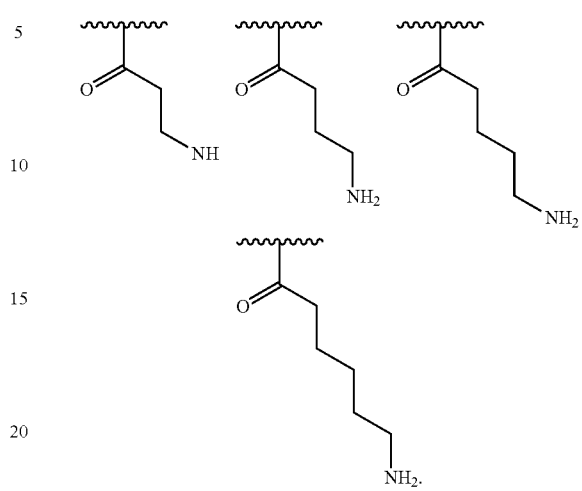

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

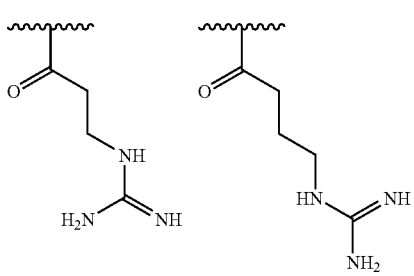

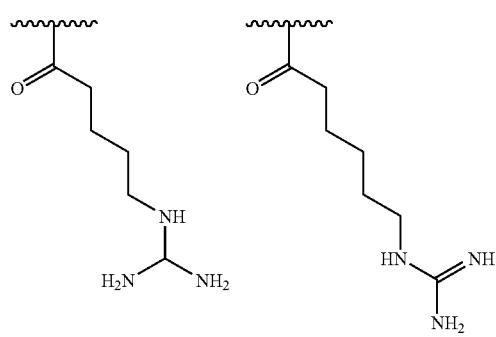

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

In another aspect, the invention features a composition for inhibiting the growth (e.g., killing) of a bacterium (e.g., MRSA) in a sample, comprising contacting the sample with an effective amount of soluble chitosan or derivatized chitosan described herein.

In some embodiments, the sample is a clinical (e.g., hospital) sample, e.g., whole blood, plasma, serum, urine, saliva, stool, sweat, tears, or stool.

In some embodiments, the bacterium is a bacterium isolated from a clinical sample, e.g., a bacterium described herein.

In some embodiments, the MRSA is selected from EMRSA15 strain, EMRSA16 strain (ST36:USA200 or MRSA252), CC8 strain designated ST8:USA300, ST8: USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the bacterium is selected from other *Staphylococcus* species such as *S. aureus, S. epidermidis, S. staprophyticus, S. lugdunensis, S. schleiferi*, and *S. caprae* and their drug resistant strains, clinical isolates from a hospital, and/or other *Staphylococcus* strains described herein.

In some embodiments, the soluble chitosan or derivatized chitosan reduces the growth rate of the bacterium (e.g., MRSA) by at least 10, 20, 30, 40, 50, 60, 70, 80, 90, 95, 99, 99.9, or 99.99%, compared to a bacteria that has not been contacted with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

formula (I)

wherein:

n is an integer between 20 and 6000; and each $R^1$ is independently selected for each occurrence from hydrogen, acetyl, and a group of formula (II):

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

In some embodiments, $R^2$ is amino and $R^3$ is a lysine side chain.

In some embodiments, $R^1$ is selected from one of the following:

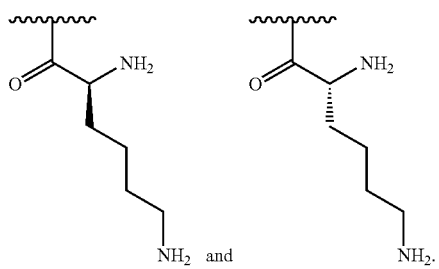 [SMILES: *C(=O)[C@@H](N)CCCCN ; "and" ; *C(=O)[C@H](N)CCCCN]

In some embodiments, $R^2$ is amino and $R^3$ is a histidine side chain.

In some embodiments, $R^1$ is selected from one of the following:

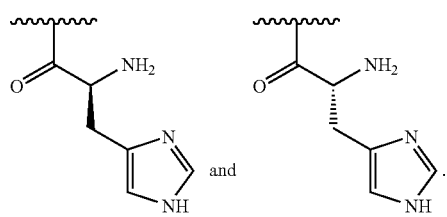 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

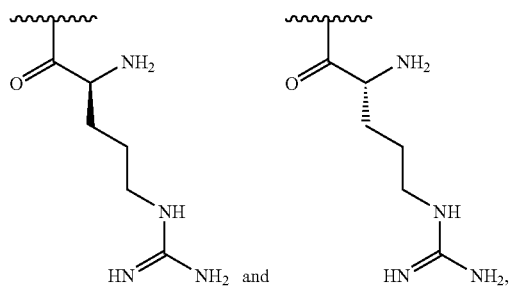

AND at least 1% of $R^1$ substituents are selected from the following:

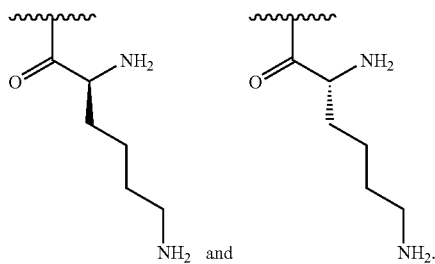 [SMILES: *C(=O)[C@@H](N)CCCCN ; "and" ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

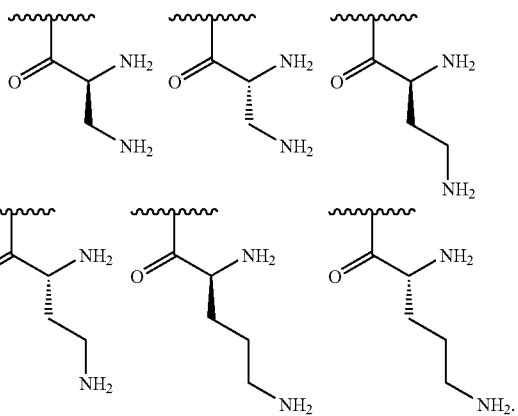

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

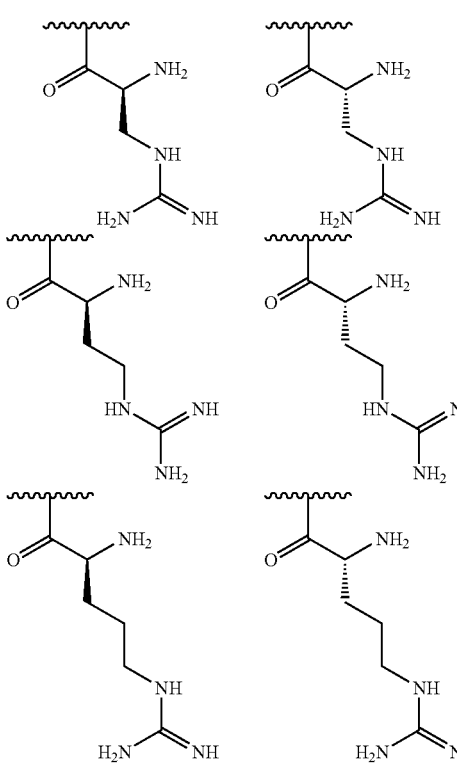

In some embodiments, $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

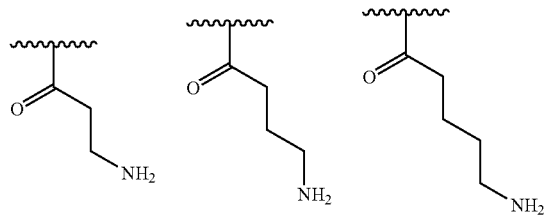

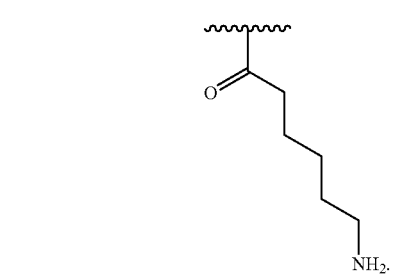

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

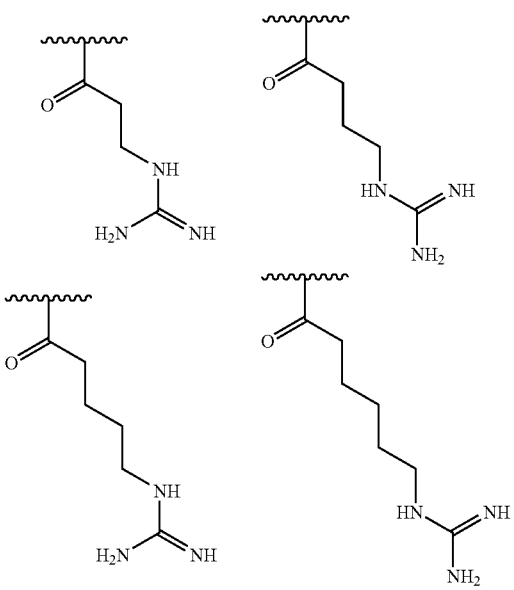

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

In yet another aspect, the invention features a kit for inhibiting the growth (e.g., killing) of a bacterium (e.g., MRSA) in a sample, comprising contacting the sample with an effective amount of soluble chitosan or derivatized chitosan.

In some embodiments, the sample is a clinical (e.g., hospital) sample, e.g., whole blood, plasma, serum, urine, saliva, stool, sweat, tears, stool.

In some embodiments, the bacterium is a bacterium isolated from a clinical sample, e.g., a bacterium described herein.

In some embodiments, the MRSA is selected from EMRSA15 strain, EMRSA16 strain (ST36:USA200 or MRSA252), CC8 strain designated ST8:USA300, ST8: USA400 strain, ST8:USA500 strain, ST59:USA1000 strain, ST59 strain, ST80 strain, ST93 strain, MW-2 strain, MNHO strain, clinical isolates from a hospital, and other MRSA strains described herein.

In some embodiments, the bacterium is selected from other *Staphylococcus* species such as *S. aureus, S. epidermidis, S. staprophyticus, S. lugdunensis, S. schleiferi,* and *S. caprae* and their drug resistant strains, clinical isolates from a hospital, and/or other *Staphylococcus* strains described herein.

In some embodiments, the soluble chitosan or derivatized chitosan reduces the growth rate of the bacterium (e.g., MRSA) by at least 10, 20, 30, 40, 50, 60, 70, 80, 90, 95, 99, 99.9, or 99.99%, compared to a bacteria that has not been contacted with the soluble chitosan or derivatized chitosan.

In some embodiments, the soluble chitosan is soluble in aqueous solution between pH 6.8 and pH 7.4.

In some embodiments, the soluble chitosan has a molecule weight less than 10,000 kDa.

In some embodiments, the derivatized chitosan comprises a chitosan of the following formula (I):

formula (I)

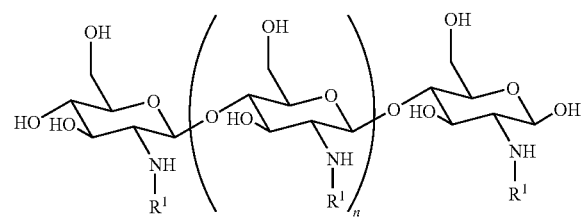

wherein:

n is an integer between 20 and 6000; and each $R^1$ is independently selected for each occurrence from hydrogen, acetyl, and a group of formula (II):

formula (II)

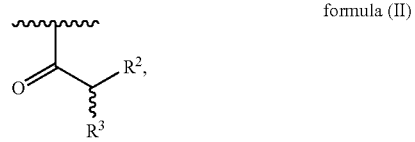

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

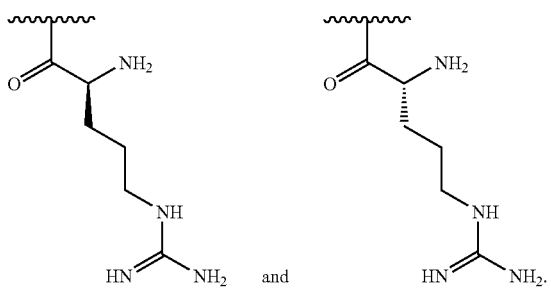

In some embodiments, $R^2$ is amino and $R^3$ is a lysine side chain.

In some embodiments, $R^1$ is selected from one of the following:

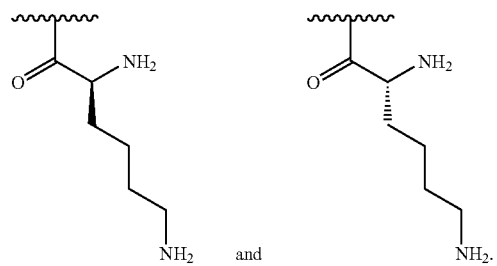 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

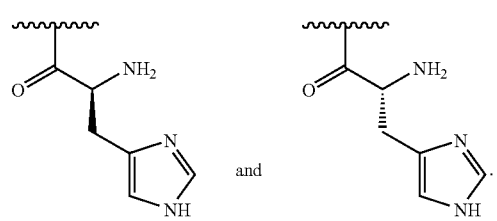 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

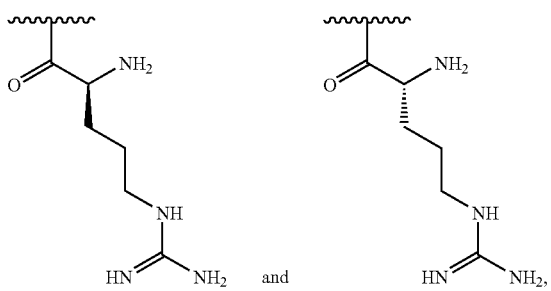

AND at least 1% of $R^1$ substituents are selected from the following:

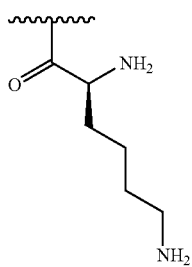 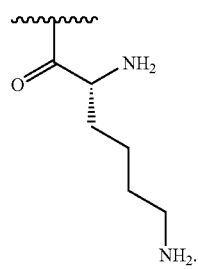

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

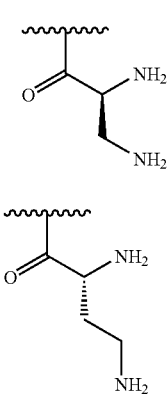 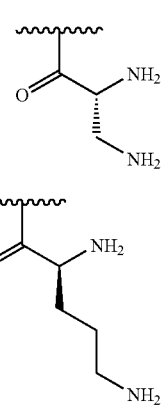 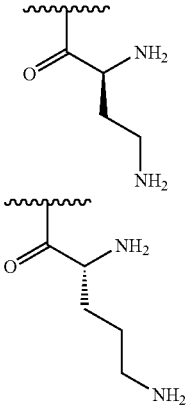

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

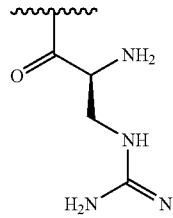 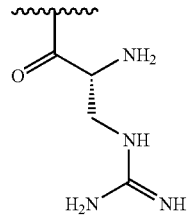

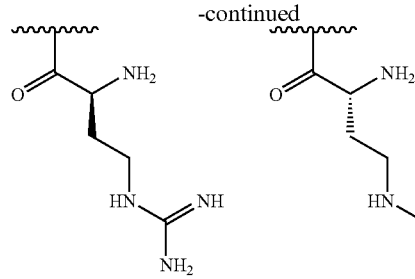

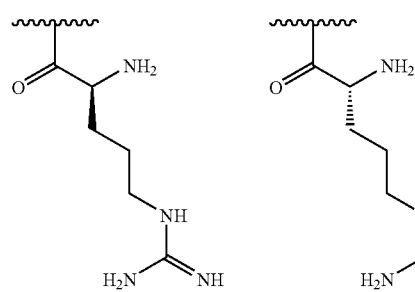

In some embodiments, $R^2$ is amino that is substituted with a nitrogen protecting group.

In some embodiments, the nitrogen protecting group is tert-butyloxycarbonyl (Boc). For example, in some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

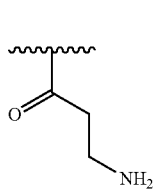 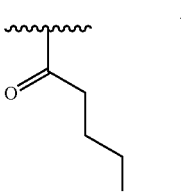 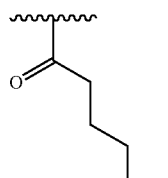

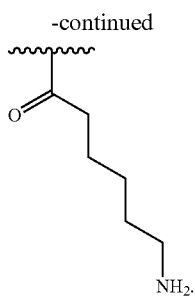

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

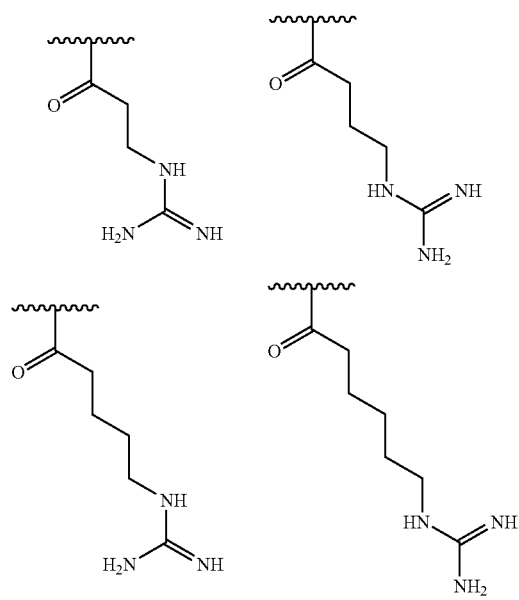

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the derivatized chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 5,000 and 60,000 Da.

In some embodiments, the molecular weight of the derivatized chitosan is between 5,000 and 35,000 Da.

In some embodiments, the derivatized chitosan is soluble in aqueous solution between pH 6.8 and pH 7.4.

In some embodiments, the derivatized chitosan is substantially free of other impurities.

BRIEF DESCRIPTION OF DRAWINGS

FIG. 1 shows planktonic killing of *Staphylococcus aureus*.
FIG. 1A shows the demonstrated bacteriocide of *S. aureus* ATCC strain 29213 at 1 hour.
FIG. 1B shows the demonstrated bacteriocide of *S. aureus* ATCC strain 29213 at 20 hours.
FIG. 1C shows the demonstrated bacteriocide of *S. aureus* ATCC strain 25923 at 1 hour.
FIG. 1D shows the demonstrated bacteriocide of *S. aureus* ATCC strain 25923 at 20 hours.
FIG. 2 shows reduction of *S. aureus* in clinical isolates in 0.1M acetate buffer at pH 7.
FIG. 2A shows demonstrated bacteriocide of MN8 at 1 hour.
FIG. 2B shows demonstrated bacteriocide of MN8 at 20 hours.
FIG. 2D shows demonstrated bacteriocide of MNHO at 20 hours.
FIG. 2G shows demonstrated bacteriocide of MW-2 at 1 hour.
FIG. 2H shows demonstrated bacteriocide of MW-2 at 20 hours.
FIG. 3 shows chitosan-arginine's ability to kill MRSA isolates.
FIG. 5 shows biofilm reduction accomplished by the addition of chitosan-arginine.
FIG. 6 shows that chitosan-arginine causes the clumping of bacteria.
FIG. 10A shows an image of the bacteria in water alone as a control.
FIG. 10B shows an image of the bacteria treated for 1 minute, at 200× magnification.
FIGS. 12A and 12B show the antibacterial activity of chitosan-arginine against MRSA in human saliva.
FIG. 13 shows the ability of various chitosan lots to clump MRSA.

DETAILED DESCRIPTION

Figure 2C:
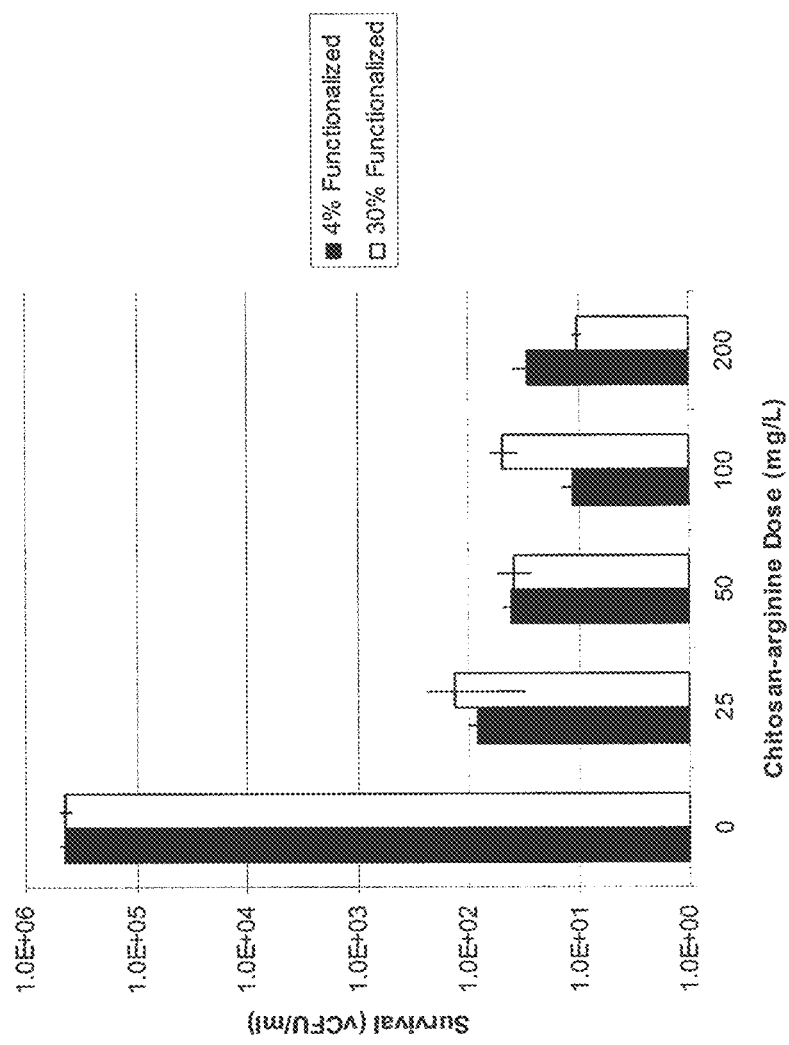
FIG. 2C shows demonstrated bacteriocide of MNHO at 1 hour.

Described herein are methods and compositions that are useful for treating or preventing bacterial infections, e.g., nosocomial infections or MRSA infections. Exemplary methods generally include use of soluble chitosans or derivatized chitosans. In some embodiments, the soluble chitosans or derivatized chitosans exhibit one or more of the following characteristics: for example, long shelf lives, ability to be stored as a dry powder, or ability to dissolve in water, saline, or other neutral solution and to be dispersed as needed.

The compounds described herein can be used to treat or prevent bacterial infections, e.g., nosocomial infections or MRSA infections. Exemplary compounds include, but not limited to soluble chitosan compounds, chitosan-arginine compounds, chitosan-guanidine compounds, chitosan-unnatural amino acid compounds, chitosan-acid-amine compounds, chitosan-natural amino acid compounds, co-derivatives of the just described compounds and the salts thereof. These compounds and their antimicrobial activity are disclosed in U.S. patent application Ser. No. 11/657,382, which is herein incorporated by reference.

The compounds described herein can be effective in the treatment and prevention of the spread of nosocomial infections or MRSA infections.

The compounds described herein can be used to treat or prevent bacterial infection, e.g., gram-positive or gram-negative bacteria. These bacteria can be across different phases of growth, e.g., biofilms attached to two different abiotic surfaces. The compounds described herein can also be more favorable in treatment and prevention of infections associated with resistant bacteria, e.g., MRSA (e.g., HA-MRSA (e.g., strain MNHO) and CA-MRSA (e.g., strain MW-2)).

Definitions

As used herein nosocomial infections refers to infection which is a result of treatment in a hospital or a healthcare service unit, but secondary to the patient's original condition. Infections are considered nosocomial if they first appear 48 hours or more after hospital admission or within 30 days after discharge. This type of infection is also known as a hospital-acquired infection (or more generically healthcare-associated infections).

As used herein resistant microorganism or bacterium means, an organism which has become resistant to an anti-bacterial agent. In embodiments a the minimum inhibitory concentration of a resistant bacterium will be at least, 2, 5, 10, or 100 greater than for that seen with a non-resistant bacterium for a selected anti-bacterial agent.

As used herein primary contact means that an individual is in direct physical contact with the subject or that they exchange bodily fluids, e.g., by drinking from the same cup. Secondary contact means that a first individual has primary contact with a second individual and the second individual has direct contact with the subject.

Treatment

The compounds described herein (e.g., a soluble chitosan or a derivatized chitosan) can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound (e.g., a compound described herein (e.g., a soluble chitosan or a derivatized chitosan) to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, the term "prevent" or "prevention" is defined as the application or administration of a compound (e.g., a compound described herein (e.g., a soluble chitosan or a derivatized chitosan)) to a subject, e.g., a subject who is at risk for a disorder (e.g., a disorder described herein), or has a disposition toward a disorder, or application or administration of the compound to an isolated tissue or cell, e.g., cell line, from a subject, e.g., a subject who is at risk for a disorder (e.g., a disorder as described herein), or has a predisposition toward a disorder, with the purpose to avoid or preclude the disorder, or affect the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, "administered in combination" or a combined administration of two agents means that two or more agents (e.g., compounds described herein) are administered to a subject at the same time or within an interval such that there is overlap of an effect of each agent on the patient. Preferably they are administered within 15, 10, 5, or 1 minute of one another. Preferably the administrations of the agents are spaced sufficiently close together such that a combinatorial (e.g., a synergistic) effect is achieved. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 20, 50, 70, or 100% greater than additive.

Functionalized Chitosan Derivatives

Methods, compounds and compositions for treating or preventing bacterial infections, e.g., nosocomial infections or MRSA infections, are described herein.

Chitosan is derived from chitin, which is a polymer of N-acetylglucosamine that is the main component of the exoskeletons of crustaceans (e.g. shrimp, crab, lobster). Chitosan is formed from chitin by deacetylation, and as such is not a single polymeric molecule, but a class of molecules having different molecular weights and different degrees of deacetylation. The percent deacetylation in commercial chitosans is typically between 50-100%. The chitosan derivatives described herein are generated by functionalizing the resulting free amino groups with positively charged moieties, as described herein. The derivatized chitosans described herein have a number of properties which are advantageous for a nucleic acid delivery vehicle including: they effectively bind and complex the negatively charged nucleic acids, they can be formed into nanoparticles of a controllable size, they be taken up by the cells and they can release the nucleic acids at the appropriate time within the cell.

Chitosans with any degree of deacetylation greater than 50% are used in the present invention, with functionalization between 2% and 50%. (Percent functionalization is determined relative to the number of free amino moieties on the chitosan polymer.) The degrees of deacetylation and functionalization impart a specific charge density to the functionalized chitosan derivative. The resulting charge density affects solubility, nucleic acid binding and subsequent release, and interaction with mammalian cell membranes. Thus, in accordance with the present invention, these properties must be optimized for optimal efficacy. Exemplary chitosan derivatives are described in Baker et al; Ser. No. 11/657,382 filed on Jan. 24, 2007, which is incorporated herein by reference.

The chitosan derivatives described herein have a range of molecular weights that are soluble at neutral and physiological pH, and include for the purposes of this invention molecular weights ranging from 5-1,000 kDa. Embodiments described herein are feature lower molecular weight of derivatized chitosans (<25 kDa, e.g., from about 5 to about 25) which can have desirable delivery and transfection properties, and are small in size and have favorable solubilities. A low molecular weight derivatized chitosan is generally more soluble than a higher molecular weight, the former thus producing a nucleic acid/chitosan complex that will release the nucleic acid and provide increased transfection of cells. Much literature has been devoted to the optimization of all of these parameters for chitosan based delivery systems.

The functionalized chitosan derivatives described herein include the following:

(A) Chitosan-arginine compounds;
(B) Chitosan-natural amino acid derivative compounds:
(C) Chitosan-unnatural amino acid compounds;
(D) Chitosan-acid amine compounds; and
(E) Chitosan-guanidine compounds.
(F) Neutral chitosan derivative compounds.

(A) Chitosan-Arginine Compounds

In some embodiments, the present invention is directed to chitosan-arginine compounds, where the arginine is bound through a peptide (amide) bond via its carbonyl to the primary amine on the glucosamines of chitosan:

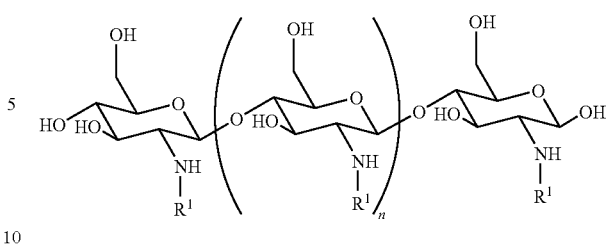

wherein each $R^1$ is independently selected from hydrogen, acetyl, and a group of the following formula:

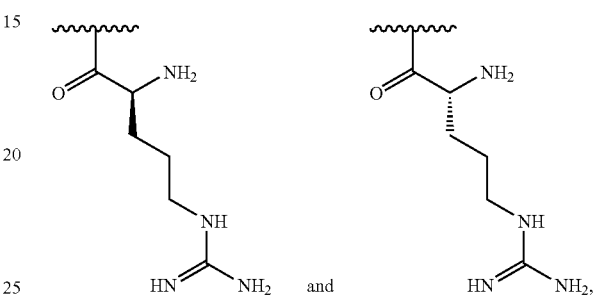

or a racemic mixture thereof, wherein at least 25% of $R^1$ substituents are H, at least 1% are acetyl, and at least 2% are a group of the formula shown above.

(B) Chitosan-Natural Amino Acid Derivative Compounds

In some embodiments, the present invention is directed to chitosan-natural amino acid derivative compounds, wherein the natural amino acid may be histidine or lysine. The amino is bound through a peptide (amide) bond via its carbonyl to the primary amine on the glucosamines of chitosan:

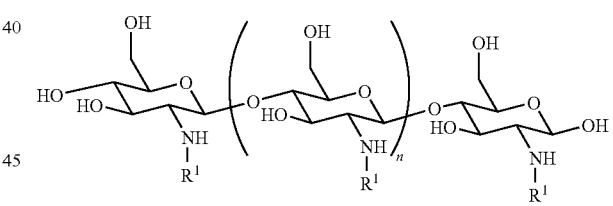

wherein each $R^1$ is independently selected from hydrogen, acetyl, and a group of the following formula:

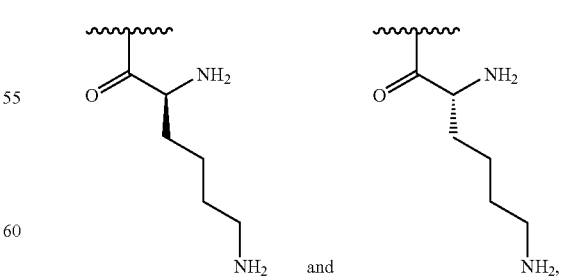

or a racemic mixture thereof, wherein at least 25% of $R^1$ substituents are H, at least 1% are acetyl, and at least 2% are a group of the formula shown above; OR a group of the following formula:

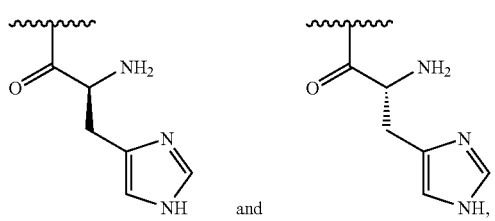

or a racemic mixture thereof, wherein at least 25% of $R^1$ substituents are H, at least 1% are acetyl, and at least 2% are a group of the formula shown above.

(C) Chitosan-Unnatural Amino Acid Compounds

In some embodiments, the present invention is directed to chitosan-unnatural amino acid compounds, where the unnatural amino acid is bound through a peptide (amide) bond via its carbonyl to the primary amine on the glucosamines of chitosan:

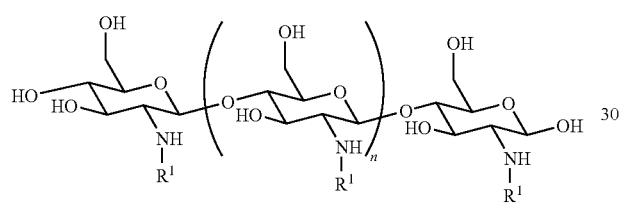

wherein each $R^1$ is independently selected from hydrogen, acetyl, and a group of the following formula:

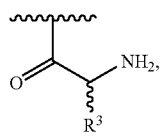

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to chitosan have the following formulae:

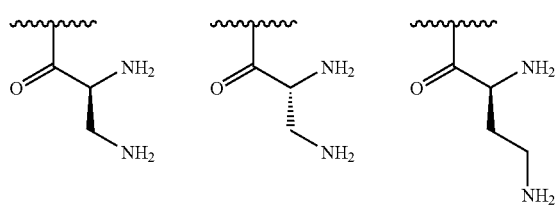

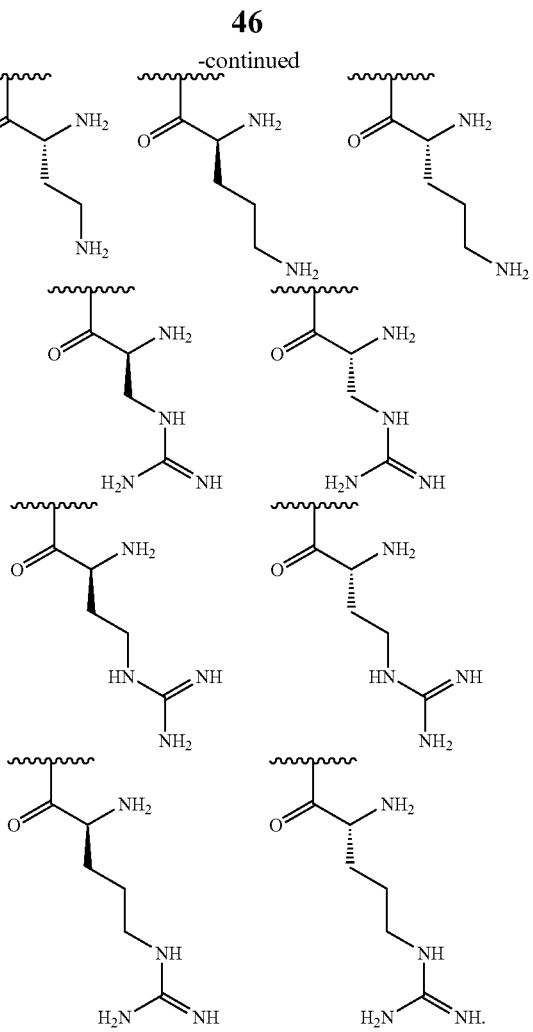

(D) Chitosan-acid Amine and Guanidine Compounds

In some embodiments, the present invention is directed to chitosan-acid amine compounds, or their guanidylated counterparts. The acid amine is bound through a peptide (amide) bond via its carbonyl to the primary amine on the glucosamines of chitosan:

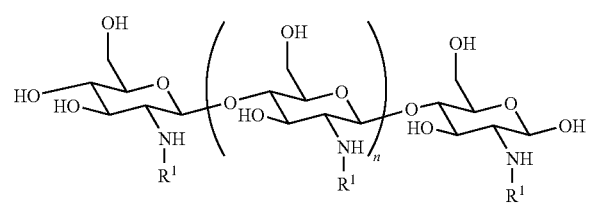

wherein each $R^1$ is independently selected from hydrogen, acetyl, and a group of the following formula:

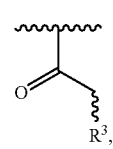

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

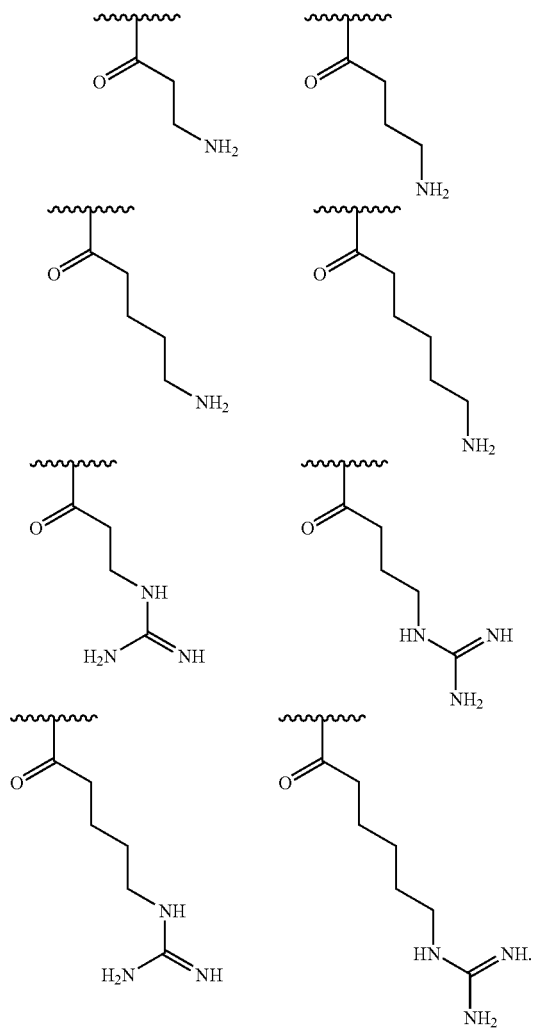

(E) Chitosan-Guanidine Compounds

In some embodiments, the present invention is directed to chitosan-guanidine compounds.

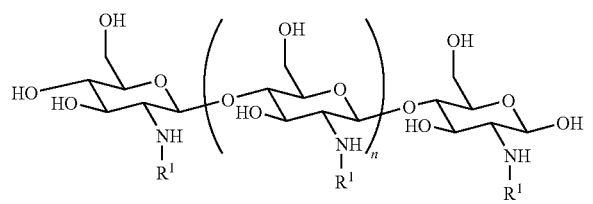

wherein each $R^1$ is independently selected from hydrogen, acetyl, and or together with the nitrogen to which it is attached, forms a guanidine moiety; wherein at least 25% of $R^1$ substituents are H, at least 1% are acetyl, and at least 2% are a group of the formula shown above.

(F) Neutral Chitosan Derivative Compounds

In some embodiments, the present invention is directed to neutral chitosan derivative compounds. Exemplary neutral chitosan derivative compounds include those where one or more amine nitrogens of the chitosan has been covalently attached to a neutral moiety such as a sugar:

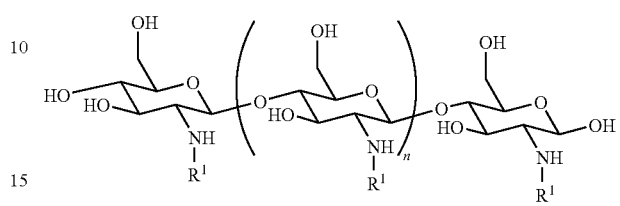

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a apacer or via the carboxylic acid, ketone or aldehyde group of the terminal sugar. Examples of α-hydroxy acids include glycolic acid, lactic acid, and citric acid. In some preferred embodiments, the neutral chitosan derivative is chitosan-lactobionic acid compound or chitosan-glycolic acid compound. Exemplary salts and coderivatives include those known in the art, for example, those described in US 20070281904, the contents of which is incorporated by reference in its entirety.

Bacterial Pathogens

Methods described herein are useful for inhibiting the growth of bacteria, e.g., bacteria that cause nosocomial infections (e.g., MRSA, such as CA-MRSA and HA-MRSA), and bacteria that are resistant to antibiotics (e.g., MRSA, such as CA-MRSA and HA-MRSA).

Exemplary nosocomial pathogens include, e.g., commensal bacteria found in normal flora of healthy humans (e.g., cutaneous coagulase negative staphylococci in intravascular line infection, and intestinal *Escherichia coli* in urinary infection), and pathogenic bacteria having greater virulence and causing infections (sporadic or epidemic) regardless of host status (e.g., Anaerobic Gram-positive rods (e.g. *Clostridium*), Gram-positive bacteria (e.g., *Staphylococcus aureus*, and beta-haemolytic streptococci), Gram-negative bacteria (e.g., Enterobacteriacae (e.g. *Escherichia coli, Proteus, Klebsiella, Enterobacter, Serratia marcescens*), and *Pseudomonas* spp.), and other bacteria (e.g., *Legionella* species).

Exemplary pathogens that cause resistant bacterial infections include, e.g., Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluorocµinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant

*Staphylococcus epidermidis.* Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagutase negative *Staphylococci*, Fluoroquinolone resistant Coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *Staphylococcus epidermidis*.

Subjects

The subject can be a human or an animal. Exemplary disorders in humans and animals include: those described above, for example as caused by an infection with a bacterium described above. Suitable animal subjects include: but are not limited to, pet, wild, zoo, laboratory, and farm animals. Suitable animal subjects include primates, rodents, and birds. Examples of said animals include, but not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

Exemplary disorders in humans include diseases characterized by the presence of one or more of the bacteria that are associated with nosocomial infections, e.g., commensal bacteria found in normal flora of healthy humans (e.g., cutaneous coagulase negative staphylococci in intravascular line infection, and intestinal *Escherichia coli* in urinary infection), and pathogenic bacteria having greater virulence and causing infections (sporadic or epidemic) regardless of host status (e.g., Anaerobic Gram-positive rods (e.g. *Clostridium*), Gram-positive bacteria (e.g., *Staphylococcus aureus*, and beta-haemolytic *Streptococci*), Gram-negative bacteria (e.g., *Enterobacteriacae* (e.g. *Escherichia coli, Proteus, Klebsiella, Enterobacter, Serratia marcescens*), and *Pseudomonas* spp.), and other bacteria (e.g., *Legionella* species).

Exemplary disorders in humans and animals also include diseases characterized by the presence of one or more of the bacteria that cause resistant bacterial infections such as Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*. Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagutase negative *Staphylococci*, Fluoroquinolone resistant Coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *Staphylococcus epidermidis*.

In some embodiments, the subject has stye, sinusitis, boils, carbuncles, furuncles, hematogenous spread, endocarditis, pneumonia, emesis, impetigo, diarrhea, scaled skin syndrome, toxic shock syndrome, urinary cystitis, and/or ostenmyelitis.

Formulations and Routes of Administration

The compounds described herein can be formulated in a variety of manners, including for oral, topical or systemic delivery (e.g., administered orally, parenterally, by inhalation spray (e.g., nasal spray), nebulizer, topically, rectally, nasally, buccally). In some embodiments, inhalation sprays (e.g., nasal spray or nasal mists), are used for the nasal delivery of a compound descried herein, either locally or systemically to treat or prevent an infection or disorder described herein, e.g., a nosocomial infection or MRSA infection. Inclusion in feed, water or an inhaled formulation is particularly desirable for use with animals.

The compounds described herein (e.g., a soluble chitosan or a derivatized chitosan) can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The compound described herein can be administered before or after the onset of the disorder described herein. The methods herein contemplate administration of an effective amount of compound or compound composition to achieve the desired or stated effect. Typically, the pharmaceutical compositions of this invention will be administered from about 1 to about 6 times per day. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound described herein or a pharmaceutically acceptable salt thereof; and a pharmaceutically acceptable carrier, adjuvant or vehicle. The compositions delineated herein include the compounds described herein, as well as additional therapeutic compounds If present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 µm to about 50 µm (e.g., from about 0.1 µm to about 10 µm, or from about 0.2 µm to about 5 µm. In some embodiments, the composition includes a dispersion of suitably-sized dry particles, for example, precipitants or crystals) or a dispersion of a solution (e.g., droplets) of a suitable size.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of compounds described herein, both the compounds are generally present at dosage levels of between about 1 to 100%, and more preferably between about 5 to 95% of the dosage normally administered in a monotherapy regimen. Additionally, combinations of a plurality of compounds described herein are also envisioned. The compounds may be administered separately, as part of a multiple dose regimen, from the compounds of this invention. Alternatively, those compounds may be part of a single dosage form, mixed together with the compounds of this invention in a single composition.

Kits

A compound described herein (e.g., a soluble chitosan or a derivatized chitosan (can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). Preferred doses, dosage forms, or modes of administration are parenteral, e.g., intravenous, intramuscular, subcutaneous, intraparenteral, bucosal, sublingual, intraocular, and topical. In another embodiment, the informational material can include instructions to administer the compound described herein to a suitable subject, e.g., a human, e.g., a human having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

In a preferred embodiment, the device is an implantable delivery device.

EXAMPLES

DDA=degree of deacetylation PDI=polydispersity

Example 1

*Staphylococcus aureus* from Culture Strains, Isolates and Clinical Isolates is Killed by Chitosan Derivatives Bacterial cultures were maintained as frozen stocks in a −80° freezer until use. The culture was thawed, and inoculated from the stock bullet at a 1:100 dilution into fresh sterile Todd Hewitt broth. The culture grew at 37° C. with shaking for 18 h in a G-76 water bath incubator. Culture OD (595 nm) is measured and bacteria were pelleted. The cells were resuspended at OD595 0.05 in 100 mM sodium acetate at pH 7.0, and 10-fold dilutions of the culture were pipetted in 100 μl aliquots into a sterile, clear polystyrene 96-well round bottom microtiter dish. After 1 h of incubation at room temperature, the culture was washed with phosphate buffered saline, washed again with Todd-Hewitt broth and resuspended in the same volume of broth Microtiter plates were centrifuged and culture fluid was removed gently with a multichannel pipetter. The plate was prepared as described previously by Brewster (2003). The prepared microtiter calibration dish was loaded into a microplate reader, and incubated at 37° C. for 18 h. Readings were taken at 595 nm with a 15 s agitation prior to each reading. The dilutions were plated on Todd-Hewitt agar to determine a corresponding growth of colony forming units for the inoculum. After the completion of the growth curve experiments, growth rates were calculated. The error for these calculations, determined as the mean value±SE, was always lower than the instrument error of 0.003 absorbance units. The time to threshold value for each dilution was plotted against initial cell concentration to determine a calibration curve. In accordance with the present invention, chitosan arginine is shown to provide bactericidal activity.

FIG. 1 shows planktonic killing of *Staphylococcus aureus*, ATCC strains in 0.1M acetate buffer at pH 7. Bacteria were incubated for 1 h (black bars) or 20 h (white bars). Bacteria were all in stationary phase of culture when tested. Data shows surviving virtual colony forming units (vCFU's) as described in the text for doses from 25 to 200 μg/ml for 51 kDa with 4% functionalization (% DDA 83, PDI 2.05); and 35.2 kDa 30% functionalized (% DDA 83) chitosan-arginine. Error is CFU+/−SE based on plate counting performed both with growth curve calibration and tests. Demonstrated bacteriocide of *S. aureus* ATCC strains 29213 at 1 hour (FIG. 1A) and at 20 hours (FIG. 1B) and of *S. aureus* ATCC 25923 at 1 hour (FIG. 1C) and at 20 hours (FIG. 1D). Note that after 20 h the levels of ATCC 25923 were below the detection limit of the assay with all doses tested (theoretically 10 cfu/ml). The strain showed sporadic growth in the microtiter wells.

Figure 2E:
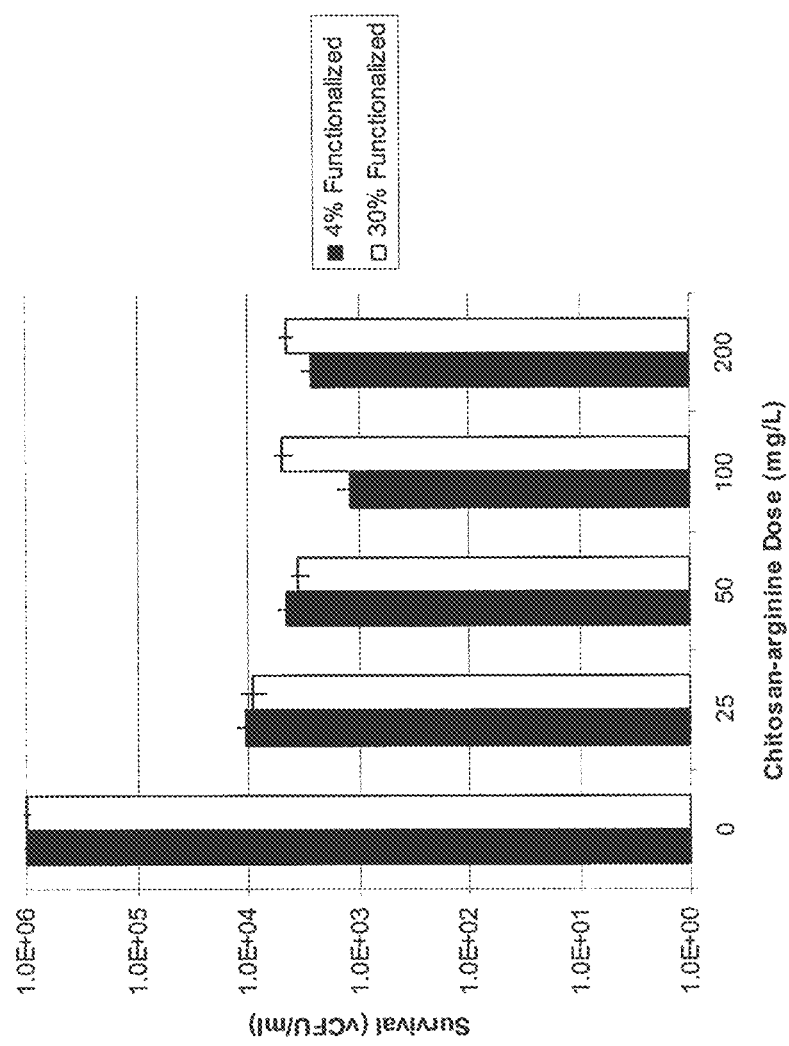
FIG. 2E shows demonstrated bacteriocide of MNDO at 1 hour.
Figure 2F:
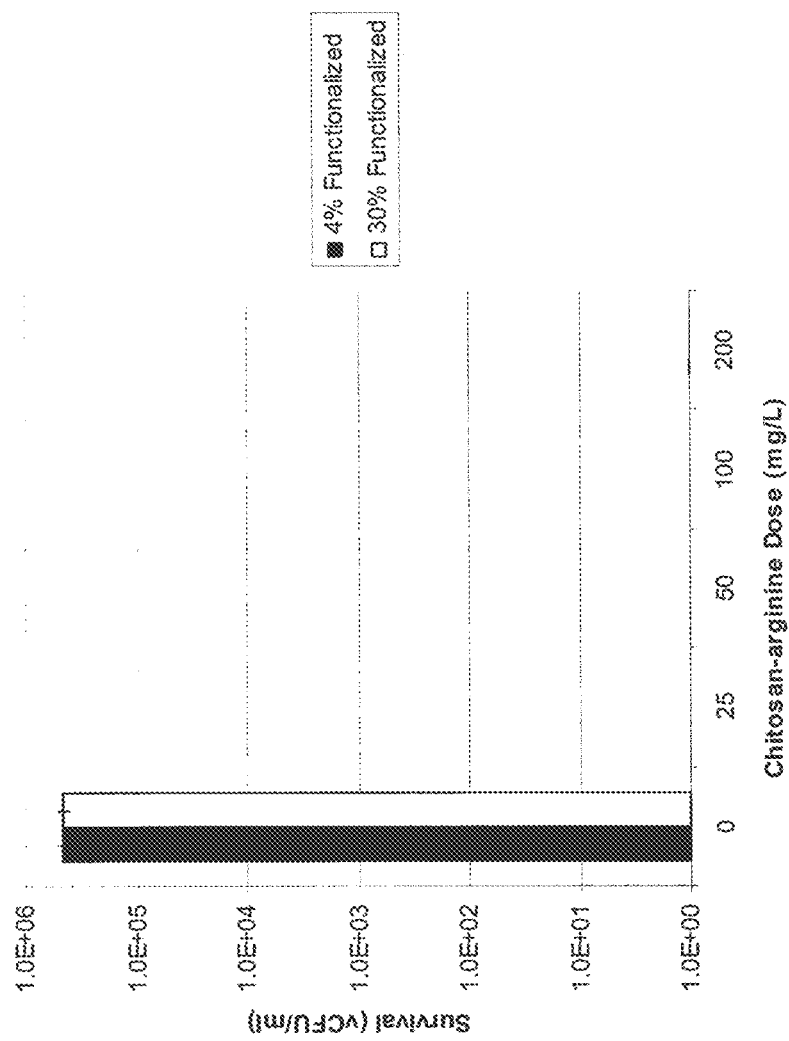
FIG. 2F shows demonstrated bacteriocide of MNDO at 20 hours.

FIG. 2 shows reduction of *S. aureus* in clinical isolates in 0.1M acecate buffer at pH 7. FIG. 2A shows demonstrated bacteriocide of MN8 at 1 hour, FIG. 2B shows demonstrated bacteriocide of MN8 at 20 hours. FIG. 2C shows demonstrated bacteriocide of MNHO at 1 hour and FIG. 2D shows demonstrated bacteriocide of MNHO at 20 hours. FIG. 2E shows demonstrated bacteriocide of MNDO at 1 hour and FIG. 2F shows demonstrated bacteriocide of MNDO at 20 hours. FIG. 2G shows demonstrated bacteriocide of MW-2 at 1 hour and FIG. 2H shows demonstrated bacteriocide of MW-2 at 20 hours. After 20 h exposure, MNDO and MN8 levels were below the assay's theoretical detection limit of 10 cfu/ml. Inferred surviving cfu below this line are reported as 10 cfu/ml. Data shows surviving virtual colony forming units (vCFU's) as described in the text for doses from 25 to 200 μg/ml for 51 kDa with 4% functionalization (% DDA 83, PDI 2.05); and 35.2 kDa 30% functionalized (% DDA 83, PDI 1.71) chitosan-arginine. Bacteria were all in stationary phase of culture when tested. Error is CFU+/−SE based on plate counting performed both with growth curve calibration and tests. Bacteria are explained in Table 1.

FIGS. 1-2 show planktonic exposure of *Staphylococcus aureus* to chitosan-arginine. The bacterial culture strains utilized include (ATCC) type strain 25923, (ATCC) strain, 29213, pathogenic *Staphylococcus aureus* strains MN8, a vaginal toxic shock syndrome (TSS) isolate, TSST-1 producer, (MNDO), a wound isolate that produces SEC, (MNHO) an methicillin resistant *Staphylococcus aureus* (MRSA(70)), a wound isolate and community-acquired methicillin-resistant *Staphylococcus aureus* (CA-MRSA) strain MW2. ATCC type strain 25923 was used for preliminary experiments to show susceptibility. The strains are listed in Table 1, below.

TABLE 1

| Bacterial species and strain | Importance | Source |
| --- | --- | --- |
| S. aureus ATCC 25923 | Initial test strain | Carolina Biologicals |
| S. aureus ATCC 29213 | Clinical isolate | |
| S. aureus MW-2 | CA-MRSA | P.M. Schlievert |
| S. aureus MNHO | Wound Isolate (MRSA, SEB) | P.M. Schlievert |

TABLE 1-continued

| Bacterial species and strain | Importance | Source |
| --- | --- | --- |
| S. aureus MNDO | Wound Isolate (SEC) | P.M. Schlievert |
| S. aureus MN8 | TSS isolate | P.M. Schlievert |
| E. faecalis | Endocarditis, VRE | Carolina Biologicals |
| Str. pyogenes | Necrotizing fasciitis | Carolina Biologicals |
| Str. pneumoniae | Meningitis, pneumonia | Carolina Biologicals |

FIG. 3 shows twelve strains of clinical isolates were acquired from Providence Medical Center (Portland, Oreg.) to test the ability of chitosan-arginine to kill a variety of MRSA clinical isolates. The MRSA were isolated from various sites of infection/colonization and included 3 each from the skin (1-3), respiratory tract/sputum (4-6), blood (7-9), and nasal orifice (10-12). A single concentration of chitosan-arginine (100 μg/mL) 28% functionalized and 23.8 kDa (% DDA 83, PDI 1.54) was used to treat approximately $10^6$ CFU/mL for 24 hours at room temperature. This dose was chosen because it is the lowest dose used for consistent and significant reductions of MRSA MW-2 in previous studies. Following treatment the cells were centrifuged and resuspended in water before being diluted and plated for CFU on Todd-Hewitt Agar plates. The CFU/mL measured are reported for each of the 12 isolates. Note that chitosan-arginine sterilized the strains as the lack of a grey bar is an indication of less than 10CFU counted.

As shown in FIGS. 1-3, chitosan-arginine is highly bactericidal against all ATCC strains, four clinical isolates tested, including the well characterized community acquired MRSA strain MW-2 and hospital acquired strains. A dose and time response was observed.

Example 2

Chitosan-arginine as a Spray Prevents MRSA Growth

Figure 4:
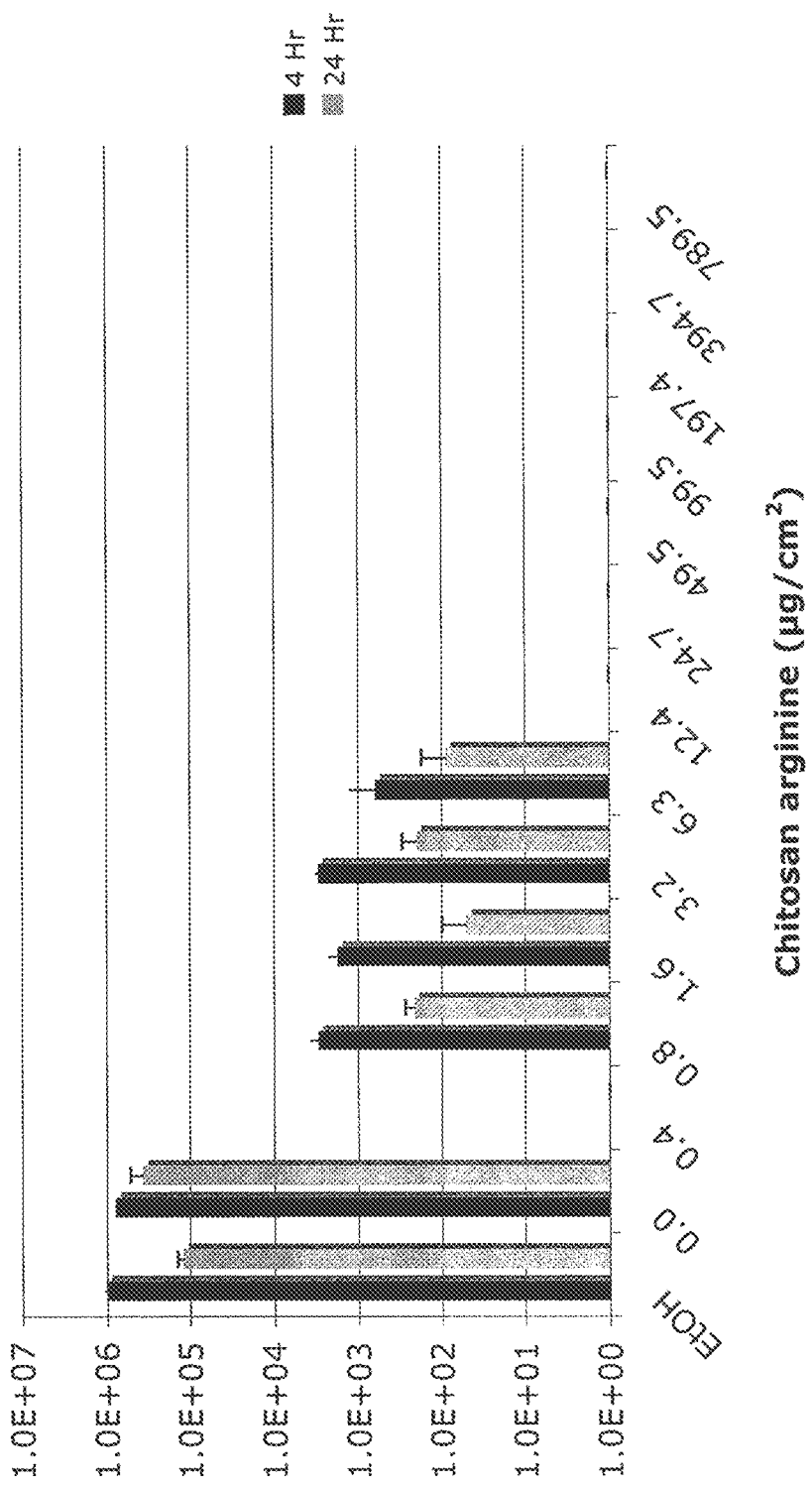
FIG. 4 shows the prevention of bacterial and biofilm growth on surfaces.

FIG. 4 shows the prevention of bacterial and biofilm growth on surfaces. Studies were completed to assess the response of methicillin-resistant *staphylococcus aureus* (MRSA) to a surface coating of chitosan-arginine. Chitosan-arginine 28% functionalized with 23.8 kDa (% DDA 83, PDI 1.54) in a solution of 90% ethanol in water was deposited with varying surface coverage to polystyrene surfaces (12-well plate) and allowed to dry completely overnight. Subsequently, $1 \times 10^6$ bacteria (200 μL of $5 \times 10^6$ bacteria/mL) of and MRSA MW-2 were deposited on the surface and recovered after 4 hour or 24 hours. The surviving bacteria were plated and counted. Note that even at very low surface coverage (<10 μg/cm$^2$), nearly complete sterilization MRSA is observed for these large bacterial challenges. FIG. 4 shows a dose response of MRSA MW-2 to a pretreatment of very low amounts of chiotsan-arginine on a surface. This prophylactic use of chiotsan-arginine is effective at preventing the growth of MRSA transferred to a surface.

Example 3

Chitosan-arginine Reduces MRSA in Preformed Biofilms

The activity of chitosan-arginine (35.2 kDa, 30% functionalized, % DDA 83, PDI 1.71) against MW-2 biofilms was assessed using a CDC biofilm reactor. The biofilms were grown in polycarbonate wells.

After 3 d of growth in a stirred, aerated batch culture, the biofilms were removed and treated with 100 µg/ml chitosan arginine in water. Alternatively, untreated samples were incubated alongside treated samples in water. All growth and treatment took place at room temperature. After exposure, samples were removed from treatment, and evaluated by plate counting and viability staining as described above. The plate counts were accomplished by scraping the outer surface of the coupons with a flat end stock stick. After thorough scraping, the stick was placed in 500 µl sterile Millipore water. The samples were diluted in phosphate buffered saline, plated on agar, and counted for growth of colony forming units. The susceptibility of MW-2 biofilms to treatment with chitosan-arginine provided dramatic results.

As shown in FIG. 5, biofilm reduction is accomplished by the addition of chitosan arginine. Chitosan-arginine was used to reduce bacteria in preformed biofilms. MW-2 biofilms were grown in Todd Hewitt broth for 2.5 days. The biofilm were washed and treated with 0, 10, 50 or 100 µg.mL of chitosan-arginine 28% functionalized, 23.8 kDa (% DDA 83, PDI 1.54) for 4 hours. The biofilms were scraped from the wells, diluted and plated to count for colony forming units, CFU. The data shows the remaining CFU after this exposure and shows up to a four log reduction in bacteria.

Example 4

Figure 6B:
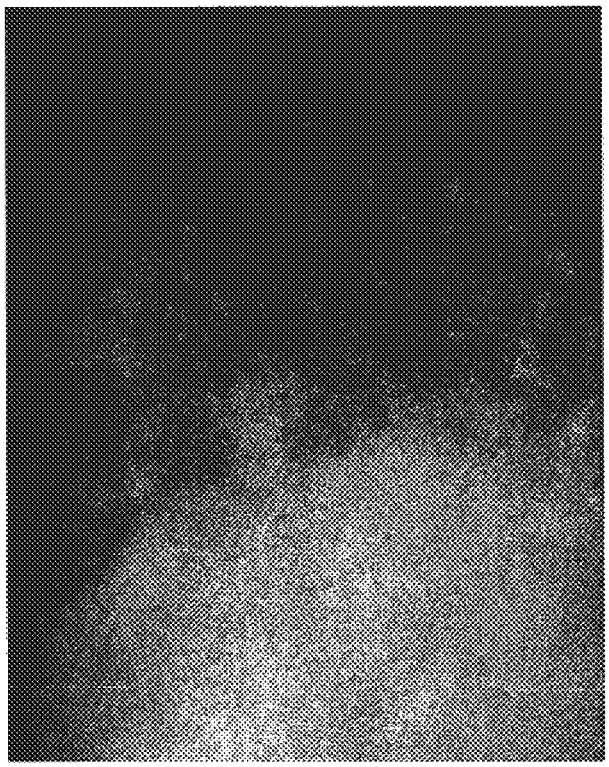
FIG. 6B shows images of the bacteria treated for 1 minute, at 400× magnification.
Figure 6A:
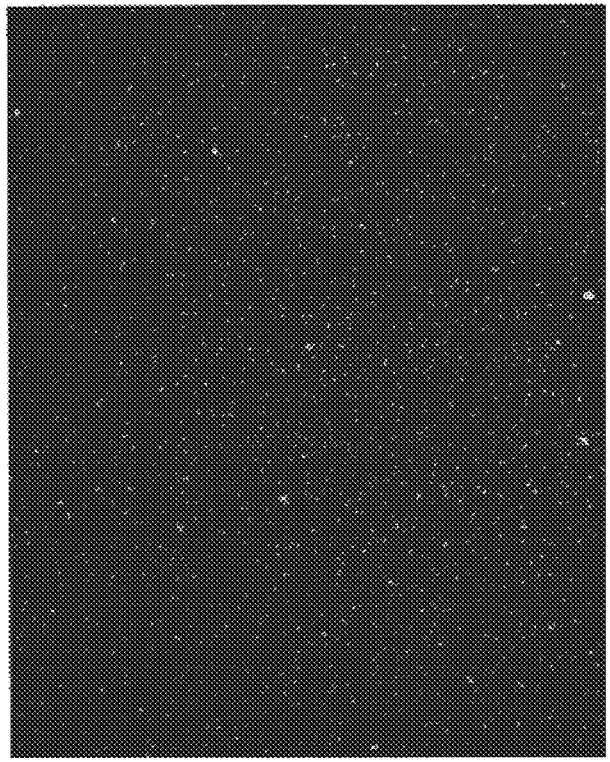
FIG. 6A shows images of the bacteria in water alone as a control.

Chitosan-arginine Clumps *Staphylococcus aureus* and Causes Membrane Permeability The methicilin resistant strain MW-2 is rapidly clumped by the addition of chitosan-arginine in solution as shown in FIG. 6. FIG. 6 shows that chitosan-arginine causes the clumping of bacteria. This physical interaction is hypothesized to facilitate aggregation and permabilization of the bacterial cell membrane. To test this hypothesis, planktonic MW-2 was treated for 1-minute with 100 µg/ml chitosan-arginine 28% functionalized, 23.8 kDa (% DDA 83, PDI 1.54) and bacteria were stained with a BacLight Live/Dead staining kit (Molecular Probes) to observe cell aggregation and determine the extent of membrane permeability. A red signal indicates that bacterial membrane permeability has increased, allowing propidium iodide to intercolate into double stranded DNA as opposed to cells labeled with the green DNA dye. The bacteria were imaged in water alone as a control as shown in FIG. 6A. FIG. 6B shows images of the bacteria or treated for 1-minute, in 400× magnification. As can be seen from the figures, this clumping occurs in less than 1 minute, which is the time limit to make the measurement.

Figure 7:
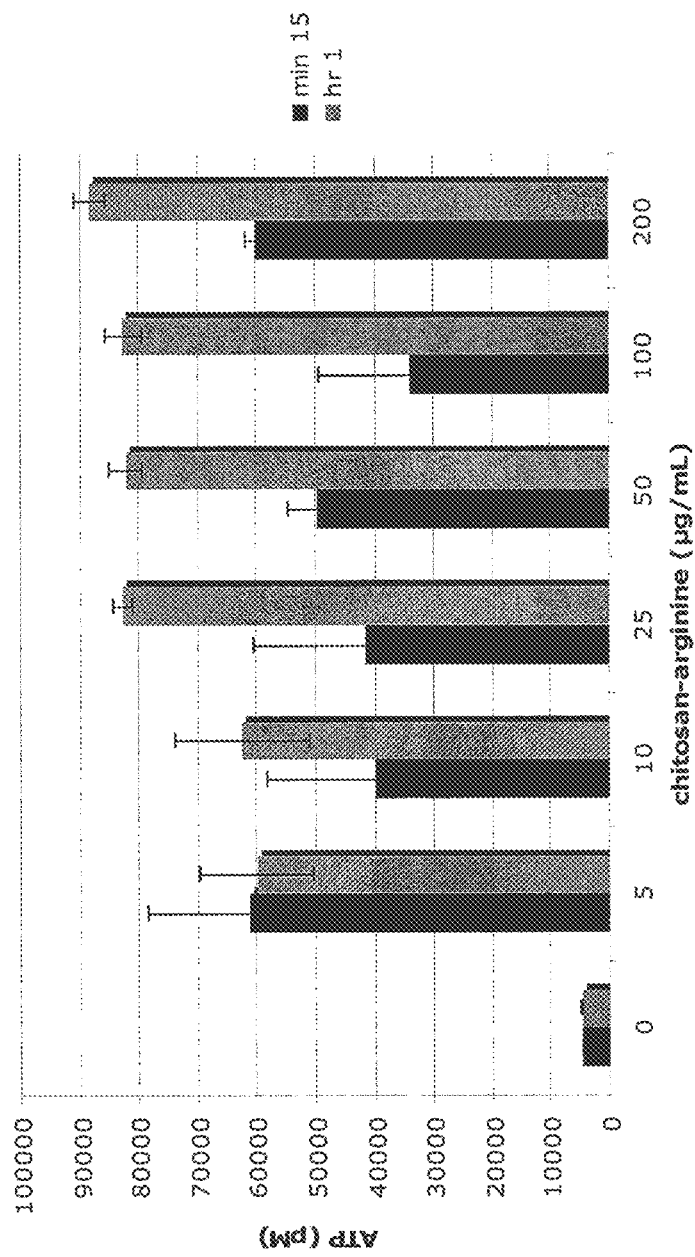
FIG. 7 shows the mechanism of bactericide is membrane disruption.

Furthermore, the bacteria become permeable, and ATP is measured outside the cell in as short as 15 minutes, the limit of our detection time for this assay, as shown in FIG. 7. The process of killing is slow, however, relative to the leakage of adenosine triphosphate (ATP). Membrane permeability was determined by measuring the amount of ATP secreted into the supernatant of a bacterial preparation of MW-2 exposed to various doses of chitosan-arginine in water with 37% functionalized, 40 kDa (% DDA 89, PDI 2.45). In this luminescence assay, ATP is measured as a function of time. FIG. 7 shows that at very low doses, the membrane leaks ATP, and that at longer time periods, more ATP has leaked out, suggesting that the time course of permeability and killing is not an instant bactericidal process.

Example 5

Lack of Resistance by MRSA to the Chitosan-derivative Compounds

Figure 8:
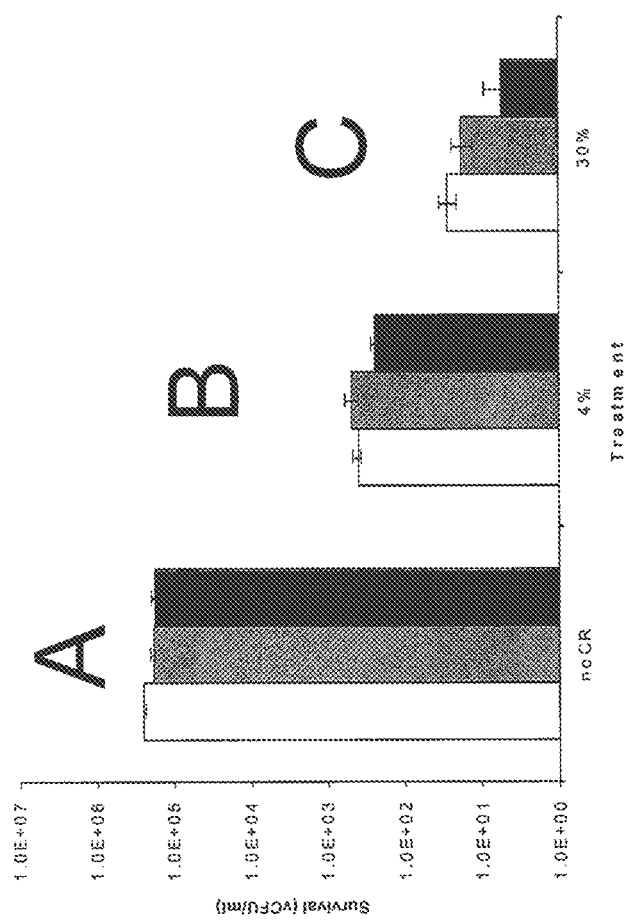
FIG. 8 shows a preliminary study to examine MRSA MW-2's ability to develop resistance to chitosan-arginine.

In accordance with the present invention staphylococci are unable to develop resistance against these chitosan derivative compounds as determined via a serial exposure and recovery experiment. When the four isolates (MW2, MNDO, MNHO, MN8) and MNHO were challenged repeatedly with chitosan-arginine (10 passages) and compared to a control that was passed repeatedly without challenge, the bactericidal efficacy of 100 µg/ml chitosan-arginine (4% and 30%) remained unchanged. FIG. 8 is a preliminary study to examine the ability of MRSA MW-2 to develop resistance to chitosan-arginine demonstrated no resistance development. The study is first divided into three groups indicated by the color of the bar to provide repetitive treatment and re-growth of surviving MRSA. Chitosan-arginine used was 51 kDa with 4% functionalization (% DDA 83, PDI 2.05) and 35.2 kDa 30% functionalized (% DDA 83). The bacteria were treated for 1-hour with either 100 mM acetate buffer alone at pH 7 (white, control), with 4% (grey) or with 30% (black) functionalized chitosan-arginine. The surviving bacteria, with a doubling time of about 30 min, were resuspended and grown to full culture over 18 hours. The treatment, rinsing and regrowth was repeated ten times in the same manner with the same treatment, so that in each iteration only the surviving bacteria were recultured, and again, challenged with the same chitosan-arginine or control. Upon completion of these ten repetitive challenges, three isolates from each of the control, 4% and 30% functionalized chitosan-arginine challenges were isolated, cultured and subjected to a final 20-hour treatment with buffer (no chitosan-arginine) in group A, 4% in group B and 30% functionalized chitosan-arginine in group C. The resulting surviving colonies were enumerated to determine if the multiple challenges reduced bacterial (MRSA) susceptibility to chitosan-arginine. Note that all surviving bacteria from the various treatments grew normally when exposed to buffer (as shown in A). All surviving bacteria from the various treatments were equally inhibited by the 4% in group B and all surviving bacteria from the various treatments were inhibited by the 30% in group C, and within the error, equally so. These data suggest that the susceptibility of MW-2 is unchanged by this level of repetitive exposure to chitosan-arginine.

As shown in FIG. 8, no alteration of susceptibility in strain MW-2 was observed, although the viability of pretreated cells under non-growth conditions (in sodium acetate buffer) was altered by serial exposure. All four clinical isolates were reduced to below the assay detection limit after 20 h exposure to 100 µg/ml irrespective of pretreatment (not shown).

Example 6

Chitosan-acid Amine has Bactericidal and Clumping Activity Against MRSA

Figure 9:
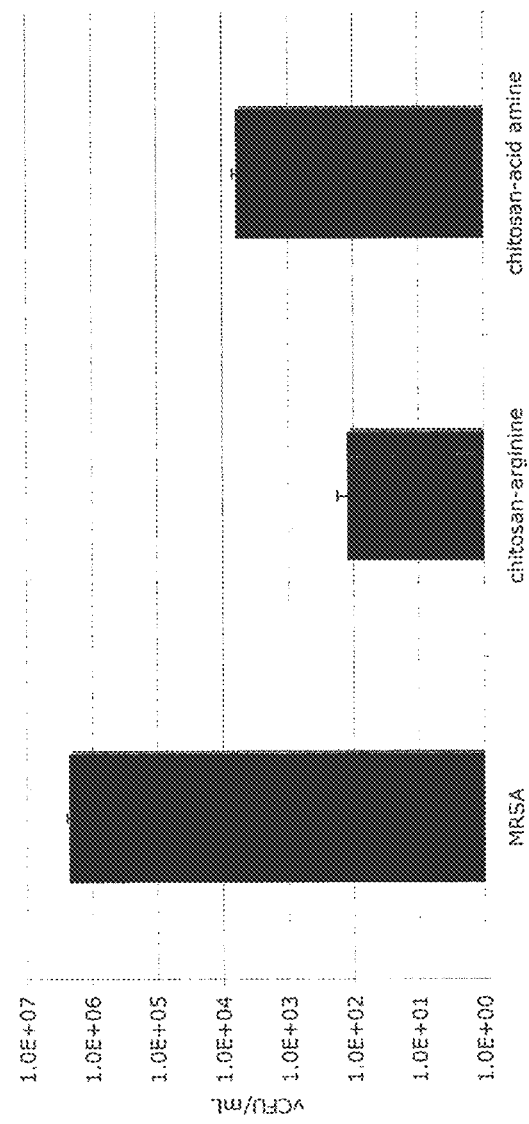
FIG. 9 shows a comparison between chitosan-acid amine and chitosan-arginine against MW-2.

Chitosan-derivatives such as the 6 amino-hexanoic acid derivative of chitosan, also show activity against MRSA. Other chitosan derivatives are active against MW-2 as well. A bacterial preparation of MW-2 was exposed to 100 mg/mL of chitosan-arginine (28% functionalized, 23.8 kDa, % DDA 83, PDI 1.54) and chitosan-acid amine (38% functionalized, 28.7 kDa, % DDA 83, PDI 1.47), 6 amino hexanoic acid) for 24 hours and virtual colony forming units as described (vCFU) were determined. While both reduce the MW-2 viability, the acid-amine derivative of chitosan for this particular strain of bacteria is less effective, but still reduces the bacterial density by three logs In FIG. 9, chitosan-acid amine is compared to chitosan-arginine against MW-2. Although its activity is not as great for planktonic growth as this particular chitosan-arginine, its MW and % functionalization have not been optimized for MW-2. Furthermore, chitosan-acid amine also clumps MW-2 as shown in FIG. 10.

Figure 10:
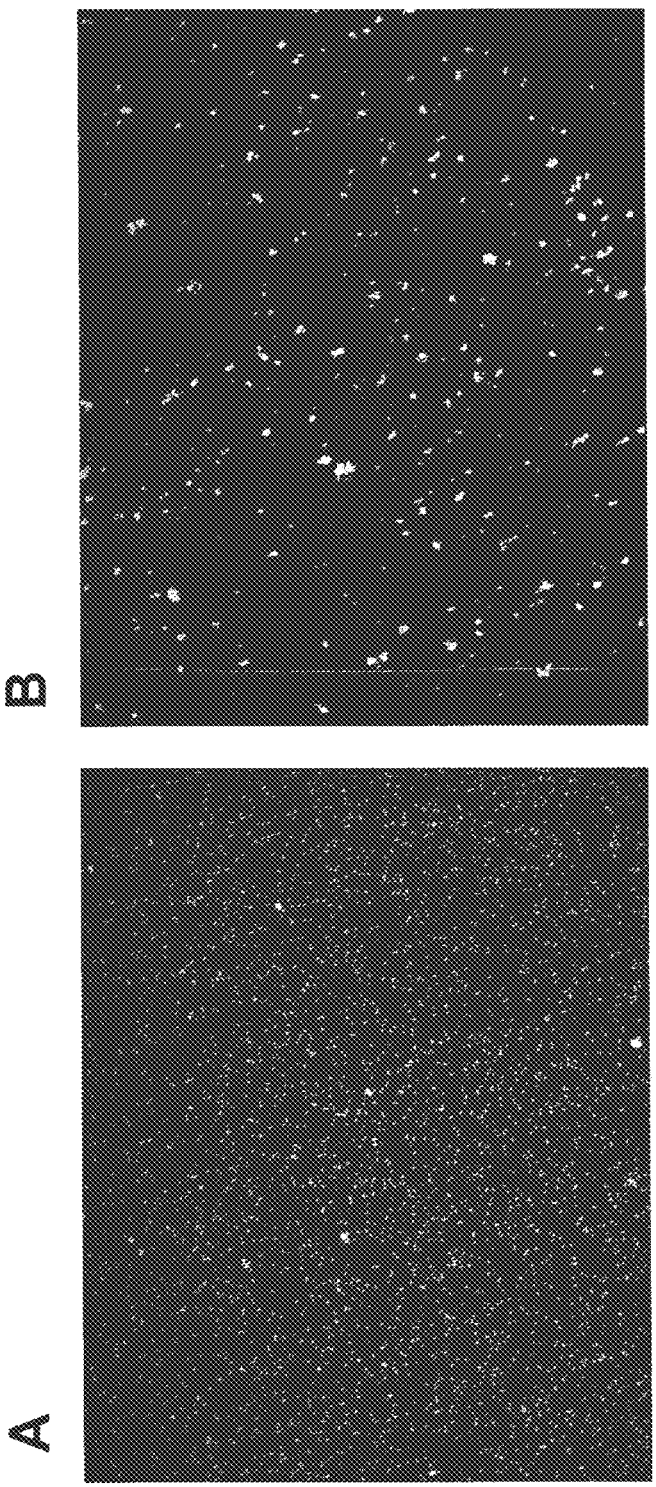
FIG. 10 shows chitosan-acid amine's ability to clump MRSA.
Figure 11:
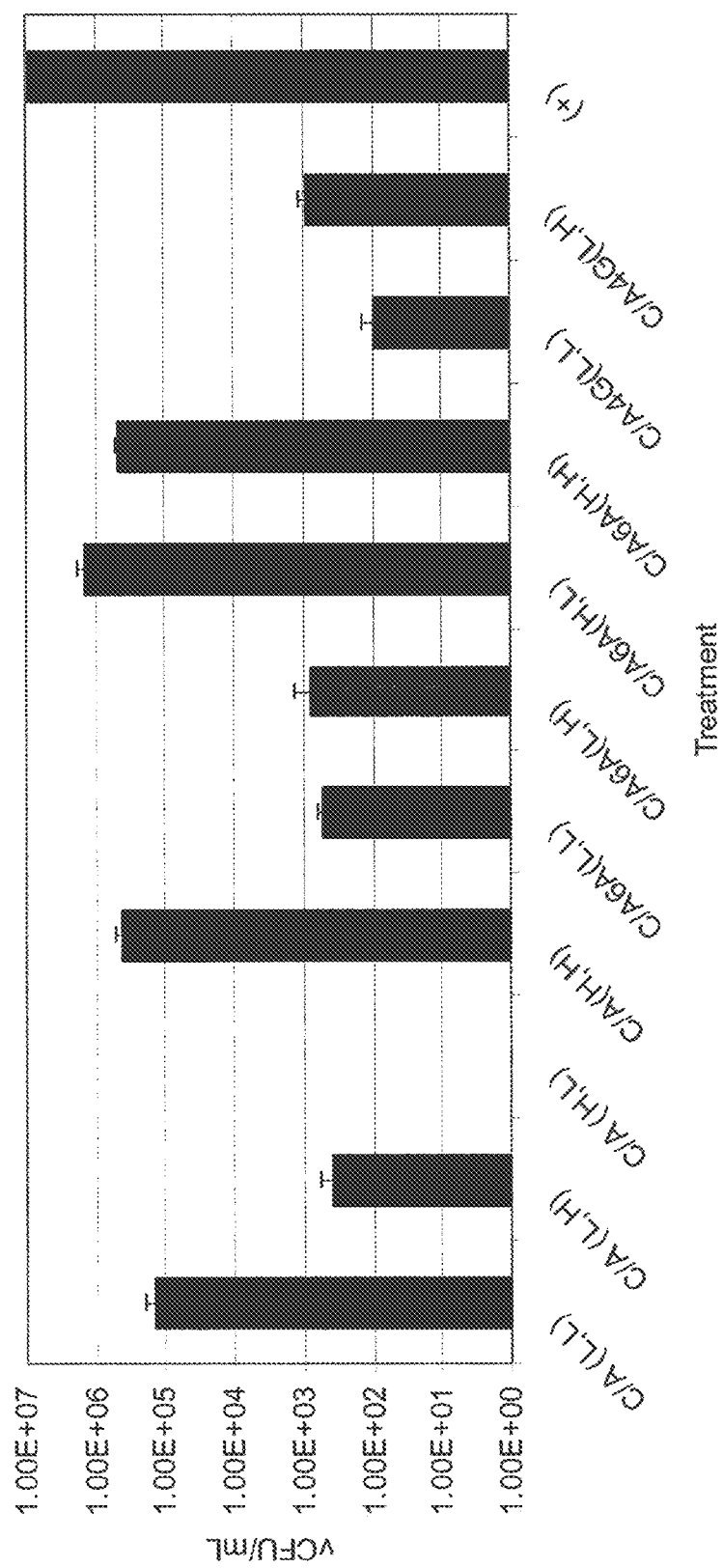
FIG. 11 shows a comparison of the antibacterial activity of chitosan derivatives against MRSA.
Figure 12A:
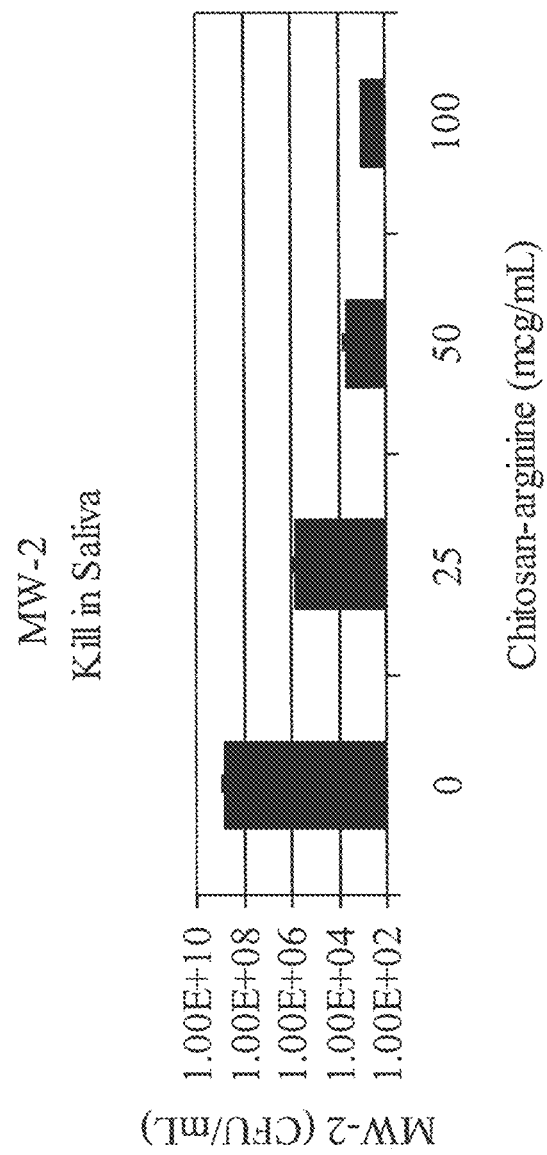

FIG. 10 shows Chitosan-acid amine's ability to clump MRSA. In this example, planktonic MW-2 was treated for 1-minute with 100 μg/ml chitosan-acid amine (38% functionalized, 28.7 kDa, % DDA 83, PDI 1.47) and bacteria were stained with a BacLight Live/Dead staining kit (Molecular Probes) to observe cell aggregation and determine the extent of membrane permeability. A red signal indicates that bacterial membrane permeability has increased, allowing propidium iodide to intercolate into double stranded DNA as opposed to cells labeled with the green DNA dye. The bacteria were imaged in water alone as a control as shown in FIG. 10A or treated for 1-minute, as shown in FIG. 10B and shown in 200× magnification. The positively charged derivatives of chitosan will have variable activity against the variety of strains of MRSA and allow for the control of MRSA populations by optimization of the derivatives relative to the strain.

Example 7

Comparative Testing of the Antibacterial Activity of Chitosan Derivatives Against MRSA The molecules comprise chitosan-arginine (C/A), chitosan-guanidinobutyric acid (C/A4G), and chitosan-aminocaproic acid (C/A6A). Standard carbodiimide coupling techniques were employed to synthesize each derivative. Each of these molecules possesses a positively charged amino or guanidinium group when dissolved in an aqueous solution at pH 7 which allows the derivative to be soluble, unlike the non-water soluble polymer chitosan which requires acid conditions for solubility.

The chitosan derivatives were comparatively tested to determine the antibacterial activity of each against Methicillin Resistant *Staphylococcus aureus* (MRSA) strain MW-2. Note that the shorthand notation of molecule such as C/A (L,H) refers to (% functionalization, MW) so that a C/A (L,H) has a low % functionalization and a higher molecular weight. The chitosan derivatives are listed in Table 2, below, each of which has DDA 89%.

TABLE 2

| | | |
|---|---|---|
| Chitosan-Arginine: | | |
| 16% | 36 kDa (PDI 2.10) | C/A (L, L) |
| 15% | 103 kDa (PDI 1.44) | C/A (L, H) |
| 31% | 52 kDa (PDI 1.35) | C/A (H, L) |
| 31% | 73 kDa (PDI 1.44) | C/A (H, H) |
| Chitosan-Aminocaproic Acid | | |
| 12% | 57 kDa (PDI 2.30) | C/A6A (L, L) |
| 12% | 126 kDa (PDI 2.12) | C/A6A (L, H) |
| 34% | 92 kDa (PDI 1.93) | C/A6A (H, H) |
| 34% | 43 kDa (PDI 1.93) | C/A6A (H, L) |
| Chitosan-Guanidinobutyric Acid | | |
| 12% | 31 kDa (PDI 2.31) | C/A4G (L, L) |
| 13% | 84 kDa (PDI N/A) | C/A4G (L, H) |

Planktonic bacteria were grown in the appropriate broth media for 18 h at 37° C., while shaking. Approximately $10^6$/ml bacteria were resuspended in water and the chitosan derivatives were added at 100 μg/ml for 4 hours to MRSA. These tests were completed in 96-well polystyrene plates in a volume of 200 μl. Following the treatment period the plates were centrifuged, supernatants were aspirated, and bacteria resuspended in the appropriate culture media and grown in the Envision 2104 multilabel reader (PerkinElmer) for 18 hours with the OD595 measure at 5 minute intervals. The time to threshold 0.25 was calculated and used to determine the vCFU following each treatment. The result is shown in FIG. 11.

Example 8

Chitosan Arginine has Antibacterial Activity Against MRSA in Human Saliva

Antibacterial activity of C/A (25% functionalization, 18 kDa, % DDA 88, PDI 1.47) against MRSA MW-2 was assessed in human saliva. The saliva was collected from one healthy donor, centrifuged, and the supernatant was stored on ice. Approximately $10^7$-$10^8$/mL MRSA were suspended in the saliva and incubated with C/A for 4 hours. The C/A concentrations used were; 0, 25, 50, and 100 μg/ml and were in a saliva solution. Results showed that C/A in saliva maintains significant antimicrobial activity (FIGS. 12A and 12B).

Example 9

Testing for the Clumping Ability of Various Chitosan Lots Against MRSA

MRSA MW-2 (5 ml) was tested for the ability of various chitosan lots to aggregate the material in water or PBS. The % DDA for each of the C/A described below is 88. C/A lots (BC04 41 kDa 26% functionalized (PDI 1.88), BC07 34 kDa 10% functionalized (PDI 2.03), BC08 18 kDa 25% functionalized (PDI 1.47), BC09 28 kDa 25% functionalized (PDI 1.71), BC10 43kDa 25% functionalized (PDI 2.28)) were tested at a concentration of 100 μg/ml. The derivatives were added to the bacterial suspensions in 15 ml plastic test tubes and 3 samples from each in a volume of 100 μl were obtained from the middle (to avoid misrepresentation of the observation because of natural bacterial settling due to gravity). A decrease in the OD 595 over time indicated the bacteria are aggregating and falling out of the suspension. The result is shown in FIG. 13. MW-2 aggregation was obvious visually after 24 hours and showed all lots were aggregating MW-2. First, MW2 was not clumping in PBS with BC08 added. Further testing showed that it was able to clump under these conditions.

Other embodiments are within the following claims.

What is claimed is:

1. A method of treating a methicillin-resistant *Staphylococcus aureus* (MRSA) infection or reducing MRSA load, the method comprising:

administering, to a subject who has a MRSA infection, an effective amount of derivatized chitosan of formula (I):

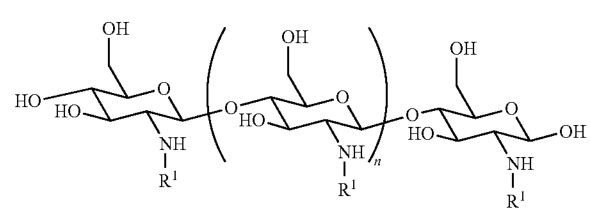

wherein:
n is an integer between 20 and 6000;
each $R^1$ is independently selected for each occurrence from hydrogen, acetyl, and a group of formula (II):

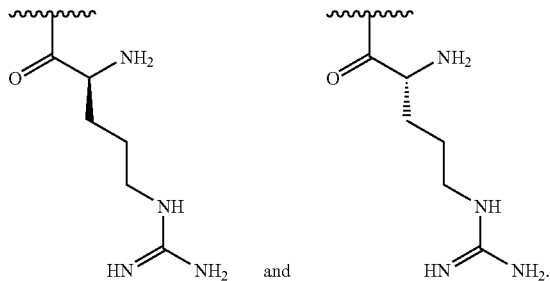

at least 25% of $R^1$ substituents are H, at least 1% of $R^1$ substituents are acetyl, and 4-30% of $R^1$ substituents are a group of formula (II); and the derivatized chitosan of formula (I) is administered at a concentration of 25-100 ppm, thereby treating the MRSA infection or reducing MRSA load.

2. The method of claim 1, wherein the subject is a human or an animal.

3. The method of claim 1, wherein the MRSA infection has previously been treated with an antibiotic without a soluble chitosan or derivatized chitosan.

4. The method of claim 1, wherein the subject has one or more symptoms selected from a group consisting of: a red, swollen and painful area on the skin, drainage of pus or other fluids from the infected site, fever, skin abscess, warmth around the infected area, chest pain, chills, fatigue, fever, malaise, headache, muscle aches, rash, wound, skin breach, and/or shortness of breath.

5. The method of claim 1, wherein the soluble chitosan or derivatized chitosan is administered topically, enterally or parenterally.

6. The method of claim 1, wherein the soluble chitosan or derivatized chitosan is administered by inhalation spray.

7. The method of claim 1, wherein the soluble chitosan or derivatized chitosan is not administered in combination with a second therapy.

8. The method of claim 1, wherein the MRSA is selected from EMRSA15 strain, EMRSA16 strain, CC8 strain designated ST8:USA300, ST8:USA400 strain, ST8:USA500 strain, ST59:USA1000 strain, ST59 strain, ST80 strain, ST93 strain, MW-2 strain, MNHO strain, or clinical isolates from a hospital.

9. The method of claim 1, wherein the soluble chitosan or derivatized chitosan reduces MRSA load in the subject by at least 10, 20, 30, 40, 50, 60, 70, 80, 90, 95, 99, 99.9, or 99.99%, compared to the MRSA load in the subject before treatment with the soluble chitosan or derivatized chitosan.

10. The method of claim 1, wherein between 25-95% of $R^1$ substituents are hydrogen.

11. The method of claim 1, wherein between 55-90% of $R^1$ substituents are hydrogen.

12. The method of claim 1, wherein between 4-20% of $R^1$ substituents are acetyl.

13. The method of claim 1, wherein 55-90% of $R^1$ substituents are hydrogen, 4-20% of $R^1$ substituents are acetyl, 4-30% of $R^1$ substituents are a group of formula (II).

14. The method of claim 1, wherein the molecular weight of the derivatized chitosan is between 5,000 and 1,000,000 Da.

15. The method of claim 1, wherein the molecular weight of the derivatized chitosan is between 5,000 and 350,000Da.

16. The method of claim 1, wherein the molecular weight of the derivatized chitosan is between 5,000 and 60,000 Da.

17. The method of claim 1, wherein the molecular weight of the derivatized chitosan is between 5,000 and 35,000 Da.

18. The method of claim 1, wherein the derivatized chitosan is soluble in aqueous solution between pH 6.8 and pH 7.4.

19. The method of claim 1, wherein the derivatized chitosan is substantially free of other impurities.

* * * * *